United States Patent [19]

Onda et al.

[11] Patent Number: 5,521,069
[45] Date of Patent: May 28, 1996

[54] GENOMIC DNA EXONS HAVING EXONS ENCODING HUMAN PITUITARY ADENYLATE CYCLASE ACTIVITY PEPTIDE WITH 38 AMINO ACIDS RESIDUES(PACAP38) AND A PROMOTER THEREOF

[75] Inventors: Haruo Onda, Ibaraki; Chiharu Kimura, Maebashi; Shoichi Ohkubo, Ibaraki, all of Japan

[73] Assignee: Takeda Chemical Industries, Ltd., Osaka, Japan

[21] Appl. No.: 76,011

[22] Filed: Jun. 11, 1993

Related U.S. Application Data

[63] Continuation-in-part of Ser. No. 47,246, Apr. 13, 1993, abandoned, which is a continuation of Ser. No. 741,676, Aug. 7, 1991, abandoned.

[30] Foreign Application Priority Data

Aug. 10, 1990 [JP] Japan ................................. 2-210327
Dec. 4, 1992 [JP] Japan ................................. 4-325372

[51] Int. Cl.$^6$ ............................ C12N 15/85; C12N 5/10
[52] U.S. Cl. ................. 435/69.1; 435/69.4; 435/240.2; 435/320.1; 536/24.1
[58] Field of Search ................. 435/69.1, 69.4, 435/240.2, 252.3, 252.33, 320.1; 536/23.5, 23.51, 24.1

[56] References Cited

U.S. PATENT DOCUMENTS 5,198,542 3/1993 Onda et al. ..................... 435/69.4

FOREIGN PATENT DOCUMENTS 0037723 10/1981 European Pat. Off. .
404034 12/1990 European Pat. Off. .
404652 12/1990 European Pat. Off. .

OTHER PUBLICATIONS

Benjamin Lewin, Genes IV, pp. 206–216 and pp. 238–239, 1987, John Wiley & Sons.
Lewin (Genes IV), 1990. p. 260, Oxford University Press or Cell Press, Cambridge.
A. Miyata, et al., Biochem. Biophys. Res. Commun. 164:567–574 (1989).
C. Kimura, et al., Biochem. Biophys. Res. Commun., 166:81–89 (1990).
K. Koves, et al., Endocrinology, 127:264–271 (1990).
L. Stryer, "Biochemistry, 3rd Edition" 1988, W.H. Freeman & Co., New York, pp. 117–140.
A. Miyata, et al., Biochem. Biophys. Res. Commun., 170(2):643–648 (1990).

Primary Examiner—Stephen G. Walsh
Attorney, Agent, or Firm—David G. Conlin; David S. Resnick

[57] ABSTRACT

Disclosed are (1) a genomic DNA of human PACAP38; (2) a DNA containing a DNA segment coding for human PACAP38; (3) a DNA of human PACAP 38 promotor; (4) a transformant carrying a vector which contains a DNA of (3) or further contains a DNA coding for a protein downstream from the promotor; and (5) a method for preparing a protein comprising cultivating the transformant described in the above (4), accumulating the protein in a culture product, and collecting the resulting protein such as mature PACAP 38. The DNA gives human PACAP 38 effectively and makes it possible to screen the chemical substance necessary for production of PACAP and is applied to experimental animals to understand their brain functions, which serves to elucidate human brain functions. Human PACAP38 can also be utilized as therapeutic agents about growth and maintenance of human brain nerves.

9 Claims, 16 Drawing Sheets

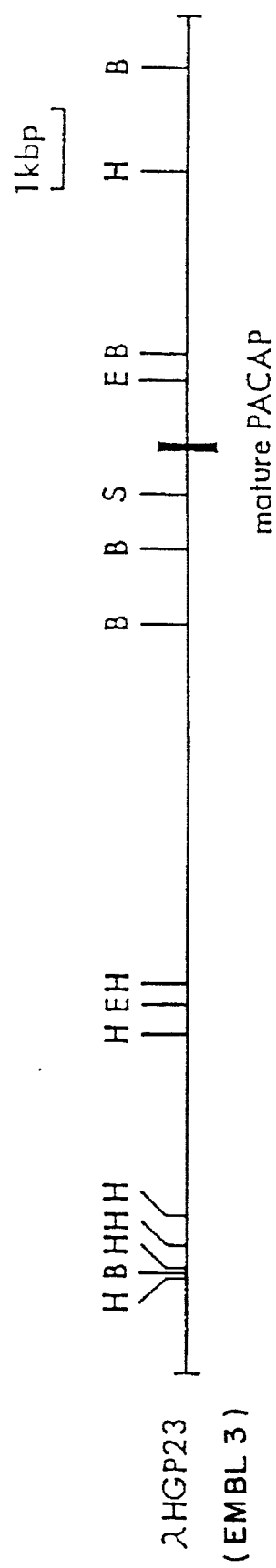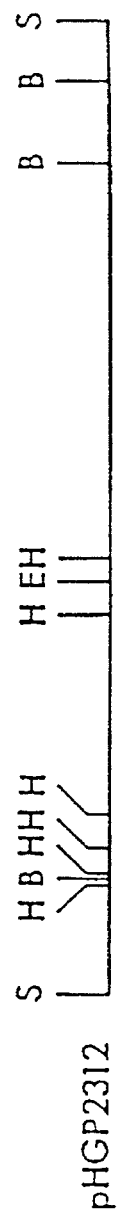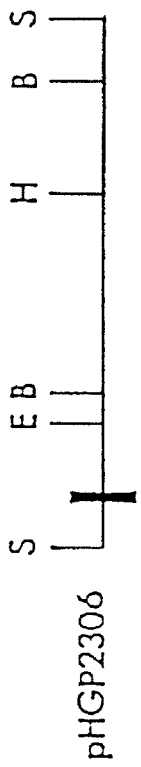
FIG. 1

```
   1  GATCACGAGGTCACGAGATCGAGAGACCATCCTGGCCAACATGGTGAAACCCCATCTCTACT
  61  AAAATACAAAAAATTAGCTGGGCATGGTGGCATGCCTGTAGTCCCAGCTACTCGGGAG
 121  GCTGAGGCAGGAGAATTGCTTGAACCCGGGAAGCGGAGGTTGCAGTGAGCCAAGATCGCA
 181  CCACTGCCTCCCCAGCCTGATGGGAGTGAGACTCCATCTCAAAAAAAAAAAAAAAAT
 241  TCCTAGAGAAATAATCTGAAGTTCAGCATTACAATGTAGCAGCTGTGTAACTTTGGAGTC
 301  ATTGAGACTTGAATCTGAAGTTCAGCATTACAATGTAGCAGCTGTGTAACTTTGGATAAG
 361  GTACCTGAGCTCTTTTAGTCCCGATTTCTTGTCTGTAAAATGGAGGTAATAACAGTGCCT
 421  ACAAAGAAGTTTGTTGTGAGGGAAAGGAAATAAGTAGTCAAGCACTTAGCCCAGGAAGTG
 481  TTCATTAAACAGTGTTGCTGTGTTGCTGTTATTCACTGGTGAATAACAAAACCATACAGTC
 541  CCTTTGGAAGGAAGGATTTAAAATAGTATTCCAAGCAGAGTATTTAAAAATTTCAACCAGT
 601  ACATTTATGACAAATGTAGAGACAAAGGATTATTTAAAAAGTATTTTCAGGTTGGGCACACTG
 661  GTGTATATTTGGGTAGAGACAAAGGATTATTTAAAAAGTATTTTCAGGTTGGGCACACTG
 721  GCTCATCCTTGCAACCCCTGCACTTGTCTCTGCAAAGTAATAACAATAATAATAAATAA
 781  GGGCAACACAGGGAGACCCTGTGGTGGCATGAGTTGAGGCTTGAGTTGCCTGTAGTCCCAGCCT
 841  AATTAGCCAGGCATGTGGTGACCCAAGAGGTTACCATACCTATATTCCCCAGGTGAGCTTGCA
 901  AGGAGTCTCACTTGGGTGACCCAAGAGGTTACCATACCTATATTCCCCAGGTGAGCTACTGCA
 961  CTCCAGCCTGGGTGACCCGTGATTACAGGTTACCATACCTATATTCCCCAGGTGAGCTACTGCA
1021  AAAACTGCAAGCAAATTATTACATGTAAACTGCTAGTAGTCCACAGGTAGATAATGCCAAGCC
1081  TCCAAATTATTACATGTAAACTGCTAGTAGTCCACAGGTAGATAATGCCAAGCCTGAGCCCAA
1141  AGGGAAGAGGATGCTAGGGCTCACAGAGGAAGACCTTCTTTTGATTTTACACACAAAA
1201  ACCTTGTTTATTTGCATATAGATTCCCCAACATTTCTGAAGTGGTCTCATTTAAGCC
1261  CTTATTAGGATATTGGTTTCCTGGATCTTTTCCTGTAGACTAAGTAAGAAGACTTCTCCTTGCATTTTA
1321  TTATGTCAGCAGAGGATTTGGAATTTGGAAGATGCTAAGCAGTGAAGTCTGAAGTCTGAAGTACATTTTG
1381  GAGGAGGTGCTCTGGAATTTGGAAGATGCTAAGCAGTGAAGTCTGAAGTCTGAAGTACATTTTG
1441  GTACCCAGTAAACTCATGTTCAGAGAAGTTAGATCCTGGTTTGTTTCTCAGATGTCTG
1501  TTGGAATCATCCAAACCTGTAGCAAAGGTTAGATCCTGGTTTGTTTCTCAGATGTCTG
1561  CTTTATATCTCAAACAAGCTTACTCATGTGGTTTGGCTCTCGTGAAGGCTTCCTTTCCTGTGTTTCA
1621  TAGATTAGAGAGAAGCACTACATTTGAAGGTCAGAGAGAAGTCATGACAGTGATAGTAAT
1681  GTGTGTGAGATGTCTCAGAGAGAAGTCATGACAGTGATAGTAATATGGTAAGCT
```

```
1741  CATCAGCTTCTTACTTCACAGTGAGTTCTGAAAGGCATGATGCATGCAGTCCAGTAAGTG
1801  ATGGTCATGATGTTCTGGTTCAGAACATTTGGGTTTCCTACAGTGTAATCGGTATGAA
1861  GTGAGTCATTAGTCATTGCATTTTCACTTTTGTCACTTTTGTCTCACACAGGAGAGAGGATAGAGAAAAGTTAAGTGAAATG
1921  TAATACAGTGTTATAATTCACTTTTGTCACAGGAGCCTGGTTCTTATGCTAAGTACTGGCATCAGG
1981  CTTGTTTACTGAAAAAGCTTATTATAGCCTGGTTCTTATGCTAAGTACTGGCTAAAAAAG
2041  AATAGAATGTGCCAGGCACGGTGGCTCACAAGGTCGAGGCACACAAGGTGGATCACAAGGTCGAGGCACACGGTGAAACCTCTGT
2101  GCAGGTGGATCACAAGGTCGAGGCACACAAAATTAGCCAGGTGTGGTGGCGTGCCCAGCTGC
2161  CTGTACTAAAAATACAAAAATTAGCCAGGTGTGGTGGCGTGCCCAGCTGC
2221  TTGGGAGGCTGAGACAGGAGAATCACTTGAACCTGGGAGGCGGAGGTTGCAGTGAGCCGA
2281  GATTGTGCCACTGCACTCCAGCCTGGGCGACAGAGCGAGACTTCATCTCAAAAAAAAAA
2341  AAAAAATGCACAACAAACATGTCTCCTTTTATATGGTTAGATTTAAGAATGTGTAGGATATAG
2401  ATGCCTTGAACAAACATGTCTCCTTTTATATGGTTAGATTTAAGAATGTGTAGGATATAG
2461  AGATAGTGGTAGTAAAAGTTAATGGGTACTATGGACTGAGCCAAAAAGAAAGTAGTGAAATCTTATCT
2521  GGAGAAACCCTGGTACTATGGACTGAGCCAAAAAGAAAGTAGTGAAATCTTATCT
2581  AAGTGACCAGAAGCCGCACTTCACTGGGGATGGAGGGCAAAATACTTTTAGCTCACC
2641  ACTGATTTGCAATATGGGAAGCCAATTCCCAAGTGTTTAAAGATGCTCAGGAACCTGGCACA
2701  GCAATATAGGGAAAGCAAACAACTATAGACATATTCCTCGTGTTTGAATACAAAAAAACCCACTTCCTCAA
2761  GACACAACAGTATATACAAACAACTATAGACATATTCCTCGTGTTTGAATACAAAAAAACCCACTTCCTCAA
2821  CTCCCAGTATATACAAACAACTATAGACATATTCCTCGTGTTTGAATACAAAAAAACCCACTTCCTCAA
2881  AGGCTAGAGTTCTTTAAATTGAATGTTAATTCAAGGTTCAAGGATTAACCTTCAACAAA
2941  GGCGGATGTGTTAGCCACCAGAAAAACAATTCGGGAAGGGTTAGTTGACTTTTAGCT
3001  ATTATTTATCATTTCTTACCCAAACTTGTTTTCACATCTGAAGGACCAACAGGATAAAAG
3061  TTGATACATTAGGGACTTGAAGTTCAGAGGCTTAGCTCACTTTCAGTTGCTGTGCCTC
3121  AAACAGCGTCTTCCCCGGCCAGGTCAGGGCTTAGCTCACTTTCAGTTGCTGTGCCTC
3181  AGGGAGGATGCTGTTAGACGTTCCAGTTAATGTAACAATCTCATAGGCTGAGCACTGCCAGCCTG
3241  GCCAAAACATGATTCCAGTTAATGTAACAATCTCATAGGCTGAGCACTGCCAGCCTG
3301  GGAATCTACTTTTCTGCCTGGAAGATTCATATCTGTAATAGAACGTTCTAACTCT
3361  GTGTTGGAAAGAAGACTTGAAATTCCTTTGTATTCGTGTAATAGAACGTTCTAACTCT
3421  TTGGTCTCTTCCTCCTCCCCCCAACCCCTCTTTGAAATTCATTTCAATTATATATATAG
```

```
3481  GAGGTTGGAAAGTTTCTCTTGAGCTCTTAACCCCAGTCACCTAAATACCCTTTGTGAGGG
3541  AAACTGGGTAAGAACAATTAAAAGTGGAAGGCTCTCCTACCCTGGTCTTGCTCTTCCCAA
3601  TTCTCCTCTAGCTCCTCCCTCCCTTATCTCTCTCTCTCTGCACTTGAAGCCAGGCTCTGA
3661  GGCTTCCTAGGATTCACCCCTCCAGCTCTGTTGGACTGGGCCACGGTATCCCACCTGCA
3721  CTTGCAATTAGTATGTCTGCCCAGCCTTGGGCTCTCTAGCCTGGGCTTTGGGCTGACAAGT
3781  CCTCCTCAGTGCATGCCGGGCATGCCCTCCTGGTCTCTCAAAGTCACACAAAGGGCATG
3841  CCCCTCTTCCTTGACTGGAGCCTTCCAAGATTAGAATCAAAGGGGCATTTGGGGTAGTTTGGT
3901  AATGCTTGAGACTTCAGTCATCCCATAGTTCCCTACCCAATAGAAAGCAGAAGGGGCCTATA
3961  CTTTGAGACTTCAGTCATCCCATAGTTCCCTACCCAATAGAAAGCAGAAGGGGCCTATA
4021  CTCTCATCTAGCAGCTTCATGAATAGGAAAGCTCTCCTGTGGGTGATCTGTAGGAGTTTGATTCCCC
4081  AAGGCCAGATTTTCATGAATAGGAAAGCTCTCCTGTGGGTGATCTGTAGGAGTTTGATTCCCC
4141  TAGACAATGGCCATGAGCAACAAAAGATCTGTGGGGTCTTTAGATGTGTTGAGCAATTGGTGGTCT
4201  CAGGCTGCTGTGGCCATGAGCAACAAAGATCTGTGGGGTCTTTAGATGTGTTGAGCAATTGGTGGTCT
4261  AGGAAGCTTGATTTTCTGGAGTTCAGTCTGAACTTGAAGGCCTGTAATTTTGGGTGAGCCCGAGT
4321  CACTCTCGTAAGTGGGTTCAGGTCTGAAGGAGAGAGCACGGGTCACAGCCTTGGTAAGTCAGAG
4381  TCTGAGCTGACAGTATCTAAGCTGACCCTGTTGGCCCTTTAATGGAGTAGTCAAGGAGTCGTT
4441  GCACAGTTCAGCCGTTTGTGGTTTCCCCTTTAATGTGAGTAGTCAAGGAGTCAGCAACATGG
4501  AATCGTGTCCCTTTACTAAAGTTGAACTCAACTCAGAACTTCGTGCGGAAGAAGCCACAGTGGGGAATAGCT
4561  TGGCTCCCTTTACTAAAGTTGAACTCAACTCAGAACTTCGTGCGGAAGAAGCCACAGTGGGGAATAGCT
4621  ATTTCTCCAGATTGAACTCAACTCAGAAGGCAAGCCACAGTGGGGAATAGCT
4681  GGGGTTCACCTTTGACGTGAAGAAAGACATCTCTGGTAGTGTTCACCGCAGGC
4741  TTGGGCGCTTTAGTAAGAAAGACATCTCTGGTAGTGTTCACCGCAGGC
4801  TCTTTGTGCGAGCTTGCTGCAGAGGCAGTGTATCAGAGAAAACACGCATGTAAACA
4861  GTCCAACATAAATCAGTGAGCATGTATCAGAGAAAAGACATATTCCCATGTAGAT
4921  GTGGTTTGAAGCTTTATTGAAGGCAGACAATCTGAAGCACGCCAGGAATAAACAAGAG
4981  GAAGCAGACAGTTTTCATTCATGGCAGACAATCTGAAGCACGCCAGGAATAAACAAGAG
5041  AGAAGGAGGAAGTATTAAATCTCAAATAAAAGCAGAACTAATAGCTTATTTAAATGTGAGATCCAAATCG
5101  AATATCTTGGAAAAAGCAAGCAGAACTAATAGCTTATTTAAATGTGAGATCCAAATCG
5161  TAGTAACAGGAAACCCCTCCCCACTAAACTGGAATTTCCCCTAATTTTTGTGTAAGATCCAA
```

FIG. 2C

```
5221  ATAATTAAAATGCACTCTAATGGTTATTGATGGCTCTATTTTCTTTCTTTCTTCTT
5281  CTTCTTTTTTTTTCAATTACCCAGGAAATTGGAAGACCTGAGTTCTCTTACTGGAGTAGAAATATAT
5341  GAACCTTCTTCAATTACCCAGGAAATTGGAAGCCTCTGGGTGGATATGTTCCCTTAT
5401  TGCTTTCCTCTCTCCCACATCATTTCAGTTAAAAAATTAACTGTTTCCAGCAGAGGAT
5461  TCCTGTGTTAGAAACCTTCATCAGGTGAACTTGTACTGGAACCCTCATGCTTTCCAGTCT
5521  GTCTGTGTCTCCCAAACAGAGCTGAAAGTGTAAACAAAGTGGAAAAACATATTTCTCACC
5581  CCAAAATTCTTAAAATTTCACTTCTTGTGAAAAGTAGCCAAACAGCCGGTCTAGAAATCAATTTTAA
5641  AATCTGTAAGAGCCACAGAAGGTGTGAAAGTAGCCAAACAGCCGGTCTAGAAATCCAAAA
5701  GCCAGGACTAACGGGGACAGAATGCTTTTCCTCAAATCCAGGCAGGGATGGGGAGCAT
5761  TCTCAGCATTAGGGCATTTATGGACGCTTATCTGAACGTTATCTGAACGGTGGGG
5821  GTGATTTAGCGATGAATCGCCACGTTAATAGCACTACTGCCAAATCTTCAAATTTAGAGG
5881  CTCTGGTGAAAAATTAAACCCGGAGTCTGGACAGCTCCCGCAGCCAGCATGAGCTCT
5941  CTTCAGCACCCGGAGTCTGGACAGCTCCGCAACGGCCAGCCAGACTCAGGAGACTCAGCTT
6001  CATCAATCTACTCATAGCCCCTTTAAAAACAAAACGACTTCCACATTTAATTAGGAGAGCTTGATGA
6061  AATCCTCCAAGACATACGCAAGAAATTAGGAGATCTAAATTGGTTGAGGCTTGATGAAGCTTGATGA
6121  AGAACATACGCAAGAGACCAGAGCTCCGATTGGTGAGGCTTGATGAAAAGTAAAGAGAAA
6181  TGCTTAATTCCAGAGACCAGAGCTCCGATTGGTGAGGCTTGATGAAAAGTAAAAATTCTTTA
6241  TCGTAATTGTATAGTTAAAACATAACTTTTGTCATCCTCAAAATTGGACTTCTTAAAAAT
6301  CCTGTCCTTGGGAAATGGAGTGAAAGGTGTTTATGAGAAGTGACTCCGGATCTTATCATCCAA
6361  TGGATTGTATGAGTGAAAGGTGTTTATGAGAAGTGACTCCGGATCTTATCATCCAA
6421  GAGGACAGCACAGAGGCTCCTTGAGGGACTAGGAGGAAGTCATTTCATGAATAAAA
6481  TGATACCCGATTCATTACGTGCAACAGTGCAACAAACCATGTTCGGCAGCAGATGTT
6541  TCGGAGCGCAACAGTGCAACAAACCATGTTCGGATAGATTTTGCACACAGATAAA
6601  GACAAAGAGGGCTCTCCAAAAACCATGTTCGGATAGATTTTGCACACAGATAAA
6661  TAGGAGCAGAAGGCCGGTCACCTCGTGTAACCAGAGCCGGTAGCGCCCGCCTCGCCCTG
6721  CAGAGGCAGCAGCCCGAGACCTCGGAGACAGAGCCGCGCCCTTGCCTCTCCTTCCCCTT
6781  GCCCGCGGCCGGCTCCTCCCTTTCCCTTCCCCTTGCCTCTCCTTTCCCCTT
6841  CTTTTCTGACTTTCCCTCTTCCCGCGCTTCACCTTACTTACGG
6901  CCACCTTGCTCTCTCCCGCCCCCATCGCCCCCTCTCTTTTCTTTCTGCCTCTCT
```

FIG. 2D

```
6961  CTGCGCCCCTTCTCTCCGTGTCACGCTCCCTCCTGGTTCTCTGCGGTCTACAAACTTTTG
7021  AGCAGAACACGAGCCTCGGCAAACGAGTCCCGCAGCTCCTCCTGCTGCTCCCGCTGGTTC
7081  CTGCGGCTTCTGCTCAGACACCAACGCCAGGGCTCCTCGGATGCCTCTCGGGTGGTGACTCCAG
7141  CGCAGGAACTTGAAGAAGCGCTTTGCCCGCCGTTCCTGGCAGCTCTCCTGGCAGCGG
7201  GAGGAGTTGAAGGGTAAGGGAGGAGGAAAATCTTACCAAAGCGACCGGCTCACTCGACTGCT
7261  GATTCTTTCGCTTGCCGTCCGCAGGGAGTTAGCTTTCCTTCAGCCGGGTCTCGGCTAG
7321  TTATTGGGCGCCGGGTAGATGCATATATATTTTTTCTAACTATAGCAAGCAAGAA
7381  GTGGCAGGGCGCGCACCGCGCTTCCAGAGCTTTGGGTTGGAGGGTGGAGCCGGGCTTCG
7441  CTCCGTCCCCTCCCCGGCTTCCTCTCTTTCCCATCCTGCGCAG
7501  TTCTCACAGCTGTGTGTCCTCTTTCCCATCCTGCGCCAG

AATGACCATGTGTAGCGGGAGCG
                                               M  T  M  C  S  G  A
7539
   1
7561  AGGCTGGCCCTGCTGGTCTATGGGATAATCATGCACAGCAGTCTACAGCTCACCTGCC
       R  L  A  L  L  V  Y  G  I  I  M  H  S  S  V  Y  S  S  P  A
7621  GCCCGGGACTCCGGTTCCCCGGGATCAG
  28   A  A  G  L  R  F  P  G  I  R

GTAGGTGCTGGCTGGCCTGCCTGGCCCAAGCAGGAG
7650  CTGGGCTCCCCAGGCACAGAGACGCTTCCTCACGGTCCTCCGGCAGTCCTTTGGGTCC
7681  AGACTACTAGCATCGCCTGCGCCCTCTGCGCCCTCGCCCAGCCTGCTCCGACGCTGGACAGC
7741  GGGTCCCCATTCTAGCAGGTCCCGGAGGTCCCGGGTAGAGCCAGTGAGCTTCTGGCCTCGGGAC
7801  CCCTAGCCAGGTCCCAACCCGGCCCACAGGATGGGGGCCAGGGAGCCCCTAGCTTTGGTTTCTTT
7861  CCTCCCCCAACCCTTGGGACGAGTTAGGAGAACTTCAGCTCTGTTCTTGTTACTGGCCTTGAGCG
7921  ACCTATTCTTGGGACGAGTTAGGAGAACTTCAGCTCTGTTCTTGTTACTGGCCTTGAGCG
7981  TGAAGCTCCCTCCACCCCTTTCTTTCATTCATTTCCCCTGAAGAGCTTTCT
8041  TCTCTCTCCCACCCTTTCTTTCATTCATTTGAATCCAGGCTGTCTTCCCCTGAAGAGCTTTCT
8101  TTCAAGTACCGTGTTCCAACTGCATTTTGAATCCCAGGCTGTCTTGGGGCCGTGCGG
8161  TGGGAGGGTGTTGGCCCGGTGTGATTGAGGAAAAGCGACTTAAGAGAGGAAGAACAAG
8221
```

FIG. 2E

```
8281  GACGAGACTGCGAAGGAGGAGGGGGAAAAACAGGCGCAAAGGAGGAGGAAGGAGAAGCCAGCA
8341  GGCAGGCAGGACCGGGAGAGCAGCCCTGCCTGGCCCCGGATGGAGAACCTTGGCTTTT
8401  TCTTAACCCCGGGTTTCTGCCAGGCGCGCGCCCAGGTTCCCGAGCCAGCCAGCCCCAGAG
8461  TCGCGGGCCGATGTGCCAGGCTGTGATGAGCCCGGGTAGGGGAGGGTTCGTACCAGCG
8521  GCGCCTGGGCAGCGAGGAGCGCGCGGCCCCGCTTCTGCCTGCCTTCCGAGCCCCGC
8581  CCAGGAACATTAGCTCTGGGGGACTGCCGCTGATCATTGATTTGGACGGAGATGGGTTCTG
8641  GGTTCTGTATTAGGATTCCAGCCATCTGGGCTGGGCTGAGGCAGGCAATATCCAGAAAGACCCC
8701  AGGGTTCGGGGTACCCGGAGGCTGAGGCGCATCGCCGAGCAAAGGCTGGGTGCGAG
8761  GCGTGCGGAATGATGCGCTTGCCTTGCCCCGGGCCCTCTCCAAGGATGGAGAAAAGGCGAGT
8821  GAAGTAGCGAAGTACGACTCCAACCCCGCCCAGAGAGTGCTACTAGCGCTGCACGC
8881  CAAGTCTCTCCAGGGTCCAAAGCGAGAGGGATTTGTTTTAACCCATCTCTACCCGTCCT
8941  GTGTCAAGAACGGAGGCTGTAGAGGGCGACTCGCGAAGTCGCCACCGCACTCGCTGGATCTC
9001  GGTCCCCTCCTCGTCGTTTAGTGGCCTTAAAAACACCCTGGTTTCACCCTCAGCTATTTCAAGTT
9061  CGAACTATTCGTTGCCTGGCCACTTTCTCCGTGCCGAGAAGCACCGAGGGTGCGACGCCACAGT
9121  CCCGTGTGCCGCCCGAACTGGCTAAGTTTAGGGGCATTTATTATTCATGTTCCTGCCAGAT
9181  CTGAGCCGCCGCCTGCCCGCCAAAATAGAAAACCGAGGTTCTCCGTGACCTACATCTGGAAGGG
9241  CCTCGCGGCGGTTCCCGGAGGCTCGGAGGCTGGGTGGGCCTCCCCGCCGTTGGCTGTTCGCGCCCA
9301  CTCCCTGGGCTCGGACCCCCCAGTCCTGGGAGAGTAGGAGTTGGTTGCTTCTTACCGGACCCTTCG
9361  CGCATCCTCTCTCCAGGCCCTTTCTGCTTTGCCTGCCGTCCCCCCGTGGGTCGCGGAGGCGCCC
9421  GGTCTCCCAGGGAGGGCCTTTTCTCGTCCCCCGCCCGCCGATCGGGAGCTCGGGAGCCAG
9481  GCGGGAGGGGGGCGGTCCCTTTTCCGTAGACAGGTGTGCGGATCGTGCCGAGACGCCTCG
9541  GTTTCCCAGCCGCTTGTTGAGCCCGGGACGACCCTTTACCCGCGAAGGGGG
9601  GTGGGCGGGACCCCCCAGTCCTGGGAGGTAGGAGTCCTGCGTTGCGTCCTTACCTC
9661  TGCTCCCACCCCAGTCCGCGAGCCCTTACTTTGGATCCTCCGCCAGCTCGGGAGGACTTTATCACCTTG
9721  TGAAAATCCGCGAGGAGCAATTCTCAGCAGGACAACAATTCTCCGCCAGCTCGGGAGGACTTTATCACCTTG
9781  GACCACACCCTTCTGTCCCCGGCCACCCCGCAG

9813  GCCAGAGGAAGAGGCGTACGGGCGAGGAC
 38   P  E  E  E  A  Y  G  E  D
```

FIG.2F

```
9841  GGAAACCCGCTGCCAGACTTCGGTGCTGGCTCGGAGCCCCCGGGGGCCCGGGGAGCCCCGCCTCC
  47   G  N  P  L  P  D  F  G  G  S  E  P  P  G  A  G  S  P  A  S
9901  GCGCCGCCGCCGCCGCCGCCGCCTGGTACCCGCCCCGGGAGAAG                     
  67   A  P  R  A  A  A  A  W  Y  R  P  A  G  R  R

9945                                             GTGAGATTCGCGCGGC
9961  CTCGCGGCACACCCGCGGCTCGGGAGCTCGGTGACGGGAGGGCCTGTCCTCTCCCTGA
10021 CCCACCCAGGATTTTTTCAGCGACAGAAATCAGCCTCAAGTCCTGGGCGGTCTGTGTGGACCTGAGGGCC
10081 CCGATCCTATTGCAGCGACAGAAATCAGCAGCGGGGCGGTCTGTGTGGACCTGAGGGCC
10141 GCGTGGGGACCCGAGGGGGGCCACTCTCTGCCCAAAGAGTGGCCAGTGAGTGGCCGTCAGCAGTTGCTCTC
10201 ACACTCCGCCATCCCGGGACTAGAGCCCGGACTAGCTCCCGATCCTCTGGAGTTTCCCTGTCAGCCTC
10261 GAGATCATCCCGGGAGTTATTGGCGAGTTCTGGGGTTTCCCTGTCAGCCCTC
10321 CCGGCCCGGCGAGGGGCGCGCGCCAACAAGGGGTCTCTAGCGCCACCTGGGACAG
10381 AAACAGTGACCCTGGGCGCGCGCACTTTGCCTCCCCCGTTAG

10420                                            AGATGTCCGCCACGGGATCCT
  82                                              D  V  A  H  G  I  L
10441 TAACGAGGCCTACCGCAAAGTGCTGGACCAGCTGTCCGCCGAAGCACCTGCAGTCGCT
  89   N  E  A  Y  R  K  V  L  D  Q  L  S  A  G  K  H  L  Q  S  L
10501 CGTGGCCCCGGGGGTGGG
 109   V  A  R  G  V  G

10519                 GTAAGAGTTTGTGTGGAAGGATTAACCTGCGCGCCGCCCGGCTGG
10561 GTGCCTGTGCGCGGGCCGGGCGGGTCTGGGGGCGGTCGCGAGGGTCCTGCCCGGAAGGTGAGT
10621 CTGCGCCCCTGGTCTGGCCAGGGAGAGCTCTGGAAGGTCGAGGTTGCCGAGATTTGAAGTG
10681 GCACTTTAAATTTGCCCAGAGAGCTCTGGAAGAGCCAAACCTCCAGCCAGGAG
10741 TTTGATCCGTTTTGAATGAAAAGAGAAAGAAACCTCCATCCAAAA
10801 CCTTCAGGCTTCCAGGAGGAGTTTTGCTATAATTTTCTAAGCATGACTGTTTCTGGGGG
10861 AGGGAAAGGGGTGGTTGTATTTACTGAAATCGAAATAATAAATGGCCAAATG
```

FIG. 2G

```
10921  TGGACACTTATGGACCCAAACAGTTTGCTCTCACGCCAGAGAAACTGAGAGCACAGGGCTT
10981  GCGTGAAGCCTATCTCGGCAGAAGGCAACATTCTAATAAAGCCCGTGGGAAAACAGATTA
11041  CATTTTCGCCATGAATAAGTCATGCGGCCTACAGCCTGTCGACTTATA
11101  TTATTATCACGTTTTTCAACTCGGCGTGAGGAGGAGAGCCAGGAGTGTTCATATTTGACTAGG
11161  AATTGCAGGATCGATGCAAACTGCAAACTCCAGGGCAGCAGACTGGCATATGTAGGGCTCTCC
11221  GGTTACTTTCTCTGTATGTCAAGGGCTGGGAGAACAGCGAGGACAATTAGCGCAAACAC
11281  ACGAAGGGTCGGATCTCAAGGGGGCGGGAGAAAGGTTAGGCTTGAAGCGCGGT
11341  CGCCTGCCCGGATCTTATCCCGAGGGGCGCCCCCGGCAGGGTTTGGTGCCAGGAGATCCTGCG
11401  TGGGGAGGGGCGACGCGGTGGGCAGTGCGAGGCCCTCCGGCTGCTTCCCGGTGGG
11461  AGGCGGGACGCCGCCTCCCCCCCCCGGGGCAGTGCGACCCCCGAAGGCTCCCGCCGTGGG
11521  GTGGGCCGCCCGCCTCCCCCCGCGATTGAACCTGTGTCTCCCCGCCCACCCTCTT
11581  CCCGACCCCTTTGCTTGCAG

11601  TGGGAGCCTCGGCGGGCCGGGGACGACGCGGAGCCG
 115    G   S   L   G   G   A   G   D   D   A   E   P

11641  CTCTCCAAGCGGCCACTCGGACGGGATCTCTTCACGGACAGCTACACCGGAAACAA
 128    L   S   K   R   H   S   D   G   I   F   T   D   S   Y   R   K   Q

11701  ATGGCTGTGCAAGAAATACTTGGCGGCCGTCCTAGGGAAGAGGTATAAACAAAGGGTTAAA
 148    M   A   V   K   K   Y   L   A   A   V   L   G   K   R   Y   K   Q   R   V   K

11761  AACAAAGGACGCCGAATAGCTTATTGTAGCGATGGGTTACCAGCTACCCTGTGTATACA
 168    N   K   G   R   R   I   A   Y   L   *

11821  GCCCTGACGGCCAATGAAAAAGTCGTTTTCCAAACTGACTCAACAGTCATCGCTCGTGTTC

11881  TATCCAAACATGTATTTATGTAATGAAGTAAAGCCATTAAATGAATATTTGATAATAAT

11941  ATTGTTTTTCTTCTACAAAGCACTAGAGAATGCACAGATATACTTTGTGGACCAATTAT

12001  TGATATATATTATAAATATATATATATAAGAATATATATATATATAAGTATAGA
```

FIG. 2H

```
12061  GAGAAGTTCATACAAAGCTGCACAAGGATTGAAAATTCGCCCGAGCTGTTTATGTTTTT
12121  ATAAAAATAAAATAGAAAAAGTAGACAATCATTGTTTGAATATTACTCCTATTTTGTAAA
12181  CTGGAATTAAAAGGATAGTATTTTTATCCATGACAGGCCTGAAGATATTACTACTTACCA
12241  TTTGCTACTGTACATAAACAATGATGCCCTGCTCCAGGAGATTTGAGGTAAAGATATG
12301  GAGAATTGCTGAAGGGCATTCTTTCCCAGTGAGTCTCTGGGCAGGCTGCTTCAATCCCA
12361  GCCTAACTCAACTGGGCTCTGTCCCCCTGGTTGGGTGGCAATTCCAATATTTCTGCTTTC
12421  TTTGATTCTCCTTTTATGTGTAGTTGTCTCTTCAGACTCTCAGCCCAGAAGAAAATTC
12481  TCCTGATAAAACAACAGCTCGATCCAAATTGTGCTTCTCCCCAGAATTCACGCCTCTCCC
12541  TAGGAGAAGAGTTGAGGAACTGTACAGAAATCTAATATCCCAAATTAGGGCAATTGGAACAAAGT
12601  TGTACTTCCTGAGTGGCCAGGAGGTATATTGGAAGAGGCAGAGCCTGAGGTGGTAGGAGGACGACCCTGG
12661  GAAGGACATAGAGGTTTGAGATTGCCCCAGGTCTGGGAAGCTGAGGCAAATCCAGTCCCAGT
12721  AAATGGACTGGTTTGAGATTGCCCCAGGTCTGGGAAGCTGAGGCAAATCCAGTCCCAGT
12781  GGTCCCTGACTTTGGGCGCTTCATCTTGTGAAATGGATGCAAAGTACAATGTGTTTTCTCC
12841  AGTGCTGTCCATGCTTCTCATCTTGTGAATGGCCAGGATCCTCCTTTGAAACCTGCT
12901  CTGTAGGAGCTACCCTTTTCCTTTGTGGTTTATGGAGACCCTTCCTCCTTCCTACCCTCCTG
```

FIG. 21

```
12961  CACTGTTTAAGTACTGTTTACCATTTTCATTCACTTCTCTTAAACTTGTGAATGCTTCT

13021  CACTTTTTTTGTTTGATGCCAGGCACTTATTGTAAATTTAGAAACCCTCTGTAGCC

13081  ACTAGTAAGTAATTATGCACTAAATATGAACCCTTTGTTTCTTGTTATTGAGTTTGTAG

13141  GTAAAATGTATTTTCTACATTATTGCTTATTGCTTAGTAAAATTTATTTCAT

AAAACCA
13198  ACCTTTGTCATATTAGAATGTGTAGTGTTCACACATGTTGCTAACTGTTTGCTAACTGATAAA
13201  TCATTTAATCCTCTCTTCATATGTATGAGTACTATCTTATATCTGTGGTCAAGAGTGAG
13261  GTAAGCAAGCTCCAACAGACCCTGAGAACCTACGCTTGTATCCTTCTTTGGCTAAAGAA
13321  AGCATGTCTGTTTCCTGTCAATTCTTTGAACATACAGAGTAATCTTTATAAACAAAAGAA
13381  CCTTCACCCAGCAATCAGATCGAGCAGCAGACAAACCAGCCAATCTCCCAAAT
13441  TTCAGGCACAAGTTTATTTTTTTTTATGTGTTTAGCTTGTAGTTAAACGTTAAGGACCTTCCT
13501  AAAAAAAAAAGAACAAGGAAAGATTAAACGTTAGCTTGTAGTTAAAGTTTAAAGGACCTTCCT
13561  TTTCCTTTACGGATTTGATCAGTATGAAGTCATAAATCAAAGAAAAACAGAATTGGATTTG
13621  CATTCCCAGGCGGGGATGGGATGCTGCCAGGAGATCAATCTTCCTTTAGTCAGTCTCC
13681  ATTCGGTCTATGCCTGAGTCCTGTATAGGATCAGCCTTTGCAGTGCAGTTAATTCCGCAGTCTCC
13741  TCAGGCAATGTGACACGGATGGCTATTTAGTGGCCCTACAATGCTGCAACACATCAGCTTGCA
13801  TGCCACGAATCACAGATTATTGTTTCTTGGATAATGGCAGAGTTTCTGTATTGTATCGAC
13861  TTTTAGTGTTTAATTATTTGTTTCTTGGATAATGGCAGAGTTTCTGTATTGTATCGAC
13921  TGTTAGTGGTGAAATAGGGCTCTAGTTAACCTTTTATTTATGAAGTCTAATTTAGTGTTC
13981  CCGTGGCTAGTTGCAAGCATTTACAGTGATCACCCAGTTTAATCTTTGTATCTTTTT
14041  AGAAATGCCAAGAGCCTTACTAAACTGAAGCAGATTTATGATATAGTAATTTAGGTA
14101  GATGTTAGTCTTGAAGCTCTTATTTGTGTGCAACTGTTGATTATAAAACACCTTAACCAAG
14161  TATTATTACACACATGAATAAATTTACTTAAACTGTGGTCTAATGTTTGGGAAAAAAG
14221  AAATTTGTATGAATAAATTTACTTAAAATCTCTTAAGTATTATATTTCTTTAGCAACCATA
14281  ACATTCAGGAAATAATTACTTTAAATCTCTTAAAGTATTATATTTCTTTAGCAACCATA
```

FIG. 2J

```
14401  AGATTTTTTACGTCTCTGGAATATATCTATCTAAGCACCCTTGTATTTCATGAACTGC
14461  ACTTTAATAATTGATGGGCAACTGGATTCTGCTAAAATTTAAAGTAGCTACTCAGATGG
14521  AGATGCCTAAGAAGGTTTAAGCTCATAAACAGGCATGATGTTGCAACATTATAAGACAC
14581  ACAATTTAGATTAATTCCATCCCCTAGTGTGTATATACTTTGCTCAATATTCAGAAAGT
14641  TACTAGGTAGTAGTGGGAGACAATGCTGTGGTTACACATCTAAAATAGCAATCT
14701  AACATTGTTCTTTATTTTAGTGGCCAGGTCTCACTAGTGTGCCAGGCTGGT
14761  CTTGCTCAAGCGATCCTCCCACCTCAGCCTCCCAAAGTGCTGGGATTACAGGCGTGAGCC
14821  ACCACACCCAGCCTAAAATAGGGATCTAACATTGTTCTTATACAAGTAACTCTGCAGACT
14881  AAACTTGTCTTGATAAAATTTTGTATAAAATGATCTCTCTGATTAAAATGCTTTAAAATCAGTTTTGGAGGTTTT
14941  AAAATGTATTTAGAGACATACAAACTACTCAAAGAGTTAATTAGATGCCTTTAAAGAAATGTACTTTGAA
15001  ACGTGAACATGAGTAAGTCATTTGTGGATTGTATGCTTTCTTAGTTCATATTTAC
15061  GTCCAGGAAGAAACACAAGAAGCTTTCTGGCTTAGAAATGTCACACATAATTGACATA
15121  AAACTTTAGGGCAAAGTTCATACGAATTCCGTAGTGGTGTGTGTTT
15181  GGCACCTTTGACTATTTCTGCCAGGGTTTCATCCTAAAAATTAAGAAGTTAATGGTCTCAATTAGTAAATC
15241  CCATTTAATTTAAAATGCCAGGATTCTAAAATTATCTCAGAAT
15301  AATAAAATATGTTACGATAGAAGGCCTAGAATGAAATCCAGTAGGAGTGAGTAGGGAGGAGCAGTTCATATTGCATTTGATTTTATTGGA
15361  TTAGCTCAGTATTTAAGGCTATTTTAAGGCCTAGAATGAATCCAGTGAACTTATTCGGTCGACTTGATAACTCAAATTCATGTATTTAGCAACTTG
15421  TTTGTAGTCAATGAAAAAAAATGAAGAAGACTTATCGGCTGACTTGGCTAGCTAATGCTATTTAGCAACTTG
15481  TAAGGAATTTTTCTTCTCCATCTTAACTGAAGACATTTGCATTTGAAGACATAGTGTGG
15541  TAGATGAAAAGATAAACCCCAGTCGGTGATAACTCAAATTACATCTTTTAAAGGCAGACTTGATACATAT
15601  CATAAAGATAAACCCCAGTCGGTGATAACTCAAATTACATCTTTTAAAGGCAGACTTGATACATAT
15661  CCATTATATCTTCGGTGATAACTCAAATTACATCTTTTAAAGGCAGACTTGATACATAT
15721  GGGTATTCAAGAAGTGCACACTTATTTGAACACGTAGTTAGGGCGCACTGGTCGAGAGAGCTT
15781  CAATACAACACCTGGGAGCTGGGAGCTTAAAACCCTGAGCTTAAAAATGTAGGACTACTGTGATCA
15841  GACTAACACCTGGGGGGGAGCTTAAAAACCCTGAGCTTAAAAATGTAGGACTACTGTGATCA
15901  TCTTTGGGGGGGAAATAAAAACCCTAGCATATGTAGGCATACATATGTGCACTAAATTTGAGACTGCCTAGA
15961  TCTGCATTTAAAATAAAAACCCTAGCATATGTAGGCATACATATGTGCACTAAATTTGAGACTGCCTAGA
16021  TAGAATTGGTGACATATGTAGGCATACATATGTGCACTAAATTTGAGACTGCCTAGATT
16081  AATAAGCAAAAGTTCATGTTACCTGCATACAGTAATAAATACATAACTGTGCCATATTCT
```

FIG. 2K

```
16141  TCCAAGATATCTGGTCATTAAGCTCTTTGACAATTTCAGTATTTCCTTTAGGTCACTAAA
16201  ACTACTAGTTAGCATTATTTTACTTGTACAGTCTGGTTGGACCTCTCCTACAGGAGCTTG
16261  TGGAAGGAGAGTGATCCTCTAAGTTGGGTCCAAAATATTCAATCACAGGACTAAGAGATT
16321  ATGGCTATAATGAGGAGAACTTGTGCAGCTAGCTAGCCATATCTGGGATCCAGAAGT
16381  CAACTTCCAGTTGCATTATATCCCAATTTGGTTTGAATGTATTTACTGCTCCCCAACTGT
16441  TTACATGATGGTTTCTCTTGGATGGCTCACTATGACCTTCAACCCTACTGTTCAC
16501  ATGATCACAAGATTGGAAGCCAAGATCAAGTCATCCCTCTGCTGCAGATTGCATCACTGCTGGATTC
16561  TTTTGTAGAAGGGAGATTGTAGTCCCTGGTCATCCTGCAACCTCCCCTGGTCACTGCAACCACATAGTTTTAGCT
16621  TTACATTGGTTTGTATCATGTCCCTCTGATCAGATGTTCCAGAGTAGCTTCCATTGTCAAAGGG
16681  CCATCTTAGTATCATGTCCCTCTGATCAGTAGTCAATCAGTGTCTTCTTCAACACGATCCTT
16741  TTAAAGGGTTTAAGGTAATCAGTAAGGGTCTTGCCTCAGGCTGGAGTGCAGTGGC
16801  CCTCTTTTTTTGTTTTTGAGAAAGGGCCTCTGCCTCCCCGGGTTTAAGCGCCCGGCTAACC
16861  ACGATCTCGCCTCACTGCAACCACAGGTTACAGGTGCATGCCCGGCTAATTTTTGTATTTTA
16921  TCCCGAGTAGCTGGGATTACAGGTGCATGCCACGCCCGGCTAATTTTTGTATTTTA
16981  GTAGAGACGGGGTTTCACTGTGTTGGCCAGGCTCTTGGACTCTCTTGTCCCCAAATGAT
17041  C
```

FIG. 2L

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 17041 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: join(7540..7650, 9814..9945, 10421..10519, 11602..11787)

( x i ) SEQUENCE DESCRIPTION: SEQ ID NO:1:

| | | | | | | |
|---|---|---|---|---|---|---|
| GATCACGAGG | TCACGAGATC | GAGACCATCC | TGGCCAACAT | GGTGAAACCC | CATCTCTACT | 60 |
| AAAAATACAA | AAAATAGCTG | GGCATGGTGG | CCCATGCCTG | TAGTCCCAGC | TACTCGGGAG | 120 |
| GCTGAGGCAG | GAGAATTGCT | TAAACCCGGG | AAGCGGAGGT | TGCAGTGAGC | CAAGATCGCA | 180 |
| CCACTGCCTC | CAGCCTGGT | GATGGAGTGA | GACTCCATCT | CAAAAAAAAA | AAAAAAAAT | 240 |
| TCCTAGAGAA | AATAAATATG | CCAGTATAAC | ATATTATAGT | CATTAAGACT | GTCTGGAGTC | 300 |
| ATTGAGACTT | GAATCTGAAG | TTCAGCATTA | CAATGTAGCA | GCTGTGTAAC | TTTGGATAAG | 360 |
| GTACCTGAGC | TCTTTTAGTC | CCGATTTCTT | GTCTGTAAAA | TGGAGGTAAT | AACAGTGCCT | 420 |
| ACAAGAAGT | TTGTTGTGAG | GGAAAGGAAA | TAAGTAGTCA | AGCACTTAGC | CCAGGAAGTG | 480 |
| TTCATTAAAC | AGTTGTTGCT | GTTGCTGTTA | TTCACTGGTG | AATAACAAAA | CCATACAGTC | 540 |
| CCTTTGGAAG | GAAGGATTTA | AATAATTTA | AACAAATAAT | CACTAAAAAT | TTCAACCAGT | 600 |
| ACATTTATGA | CAAATGTAAT | AGTATTCCAA | GCAGATGATA | GTTTTAAAA | ATTTATGCCT | 660 |
| GTGTATATTT | GGGTAGAGAC | AAAGGATTAT | TTAAAAGTA | TTTTCAGGTT | GGGCACACTG | 720 |
| GCTCATCCTT | GCAACCCCTG | CACTTTGGGA | GGCTTGAGTC | CAGGAGTTTG | TGACCAGCCT | 780 |
| GGGCAACACA | GGGAGACCTT | GTCTCTGCAA | AGTAATAATA | ATAACAATAA | TAATAAATAA | 840 |
| AATTAGCCAG | GCATGGTGGT | GGCATGTGCC | TGTAGTCCCA | GGTATTCAAG | AGGTTGAGGC | 900 |
| AGGAGTCTCA | CTTAAGCCCA | AGAGTTTGAG | GTTGCTGTGA | GCTATGAATG | CACTACTGCA | 960 |
| CTCCAGCCTG | GGTGACCGAG | GAAGACTCAG | TAAAACAAA | ACAAACAAA | CAAACAAACA | 1020 |
| AAAACTGCAA | AGCCGTGATT | ACCATACAGT | GCTAGTAATA | ATGATAATAA | AAACAAAGGC | 1080 |
| TCCAAAATTA | TTACATGTAA | ACCTATATTC | ACAGGTAGAT | AATGCCAAGC | CTGAGCCCAA | 1140 |
| AGGGAAGAGG | GATGCTAGGG | GCTCACAGAG | GAAGACCTTC | TTTTGATTTT | ACACACAAAA | 1200 |
| ACCTTGTTTT | ATTTTGCATA | TAGATTCCCC | TTCCAACATT | TTCTGAAGTG | GTCTCAAAAG | 1260 |
| CTTATTTAGG | ATATTGGTTT | TCCTGGATCC | TGTCCAAGCT | TTTCCTTCTG | CATTTAAGCC | 1320 |
| TTATGTCAGC | AGAGGATTTA | GACTAAGTAG | AGAGAAGACT | TTCTTCTCCT | TGGCTTTTTA | 1380 |
| GAGGAGGTGC | TCTGGAATTT | GGAAGATGCT | ACACAGTGAA | GTCTGGGATA | TACATTTTTG | 1440 |
| GTACCCAGTA | AACTCATGTT | CAGAGAATAA | GGCCTTAGTA | GAGCCATATA | TGTGAGATAT | 1500 |
| TTGGAATCAT | CCAAACCTGT | AGCAAAGGTT | AGATCCTGGT | TTTTGTTTCT | CAGATGTCTG | 1560 |
| CTTTATATCT | CAAAACAACA | AGCAAAATTT | CTTGGCTCTG | TGAATATGCA | ATTCTGTTCT | 1620 |
| TAGATTAGAG | AGAAGCTTTA | CTCATGTGGT | TTGGAAGGCT | TCCTTTCCTA | GTTGTTTTCA | 1680 |

```
GTGTGTGAGA AGCACTACAT TTTGAAGGTC AGAGAAGTCA TGACACATTA TAGGTAAGCT   1740
CATCAGCTTC TTACTTCACA GTGAGTTCTG AAAGGCATGA TGCATGCAGT CCAGTAAGTG   1800
ATGGTCATGA TGTTCTGGTT CAGAACATTT GGGTTTCCCT ACAGGTGTAA TCGGTATGAA   1860
GTGAGTCATT AGTCATTGCA TTTTCTGGAA AAGTCGGTAG AGAAAAGTTT AAGTGAAATG   1920
TAATACAGTG TTATAATTCA CTTTTGTCAC TCACAGGAGA GGATGATGTT TTGCATCAGG   1980
CTTGTTTACT GAAAAAGCTT ATTATAGCCT GGTTCTTATG CTAAGTACTG GCTAAAAAG    2040
AATAGAATGT GCCAGGCACG GTGGCTCACG CCTGTAATCC CATTACTTTG AAAGGCTGAG   2100
GCAGGTGGAT CACAAGGTCA GGAGTTCGAG ACCAGCCTGG CGAACACGGT GAAACTCTGT   2160
CTGTACTAAA AATACAAAAA TTAGCAGGGT GTGGTGGTGG GTGCCTGTAG TCCCAGCTGC   2220
TTGGGAGGCT GAGACAGGAG AATCACTTGA ACCTGGGAGG CGGAGGTGGC AGTGAGCCGA   2280
GATTGTGCCA CTGCACTCCA GCCTGGGGGA CAGAGCGAGA CTTCATCTCA AAAAAAAAA    2340
AAAAAATGC ACAACTTTTC CAATCTTGAT TTAGATTATT TATACTAGGA ATGTGTGAGG    2400
ATGCCTTGAA CAAACATGTC CTTTTATATG GTTAAGAAAA TCAAATGTTG TAGGATATAG   2460
AGATAGTGGT AGTAAAAGGT AATGGTGTAG AGATATGTAC CTAAGGAAAG AGAATGTCAT   2520
GGAGAAACCC TGGGTACTAT GGGTGACTGA GCCAAAAGA AAGTAGTGGA AATCTTATCT    2580
AAGTGACCAG AAGCCGCACT TCACTGGGCT GCTTAAAGGC AAAAATACTT TTAGCTCACC   2640
ACTGATTTGC AATATGGGGA TGGAGGGGAG CAGTGTTTAA AAGATGCTGA AGATTCCCAT   2700
GCAATATAGG GAAAGCCAAT TTCCCAAGTG GTGATGGTCC AAAGGCAGGA ACCTGGCACA   2760
GACACAACAG TACAAACACT ATAGTATTTG CTAATGTTGT GAAGCCATCT GCAATTCAAA   2820
CTCCCAGTAT ATATACTAGA CATATTCCTC CTGTTTGAAT ACAAAACCC ACTTCCTCAA    2880
AGGCTAGAGT TCTTTAAATT GAATGTTAAT TCAAGGTTCA AGGATTAACC CTTCAACAAA   2940
GGCGGATGTG TTAGCCACCA GGAAAAACAA TTCGGGGAAG GGTTAGTTTG ACTTTTAGCT   3000
ATTATTTATC ATTTCTTACC CAAACTTGTT TTCACATCTG AAGGACCAAC AGGATAAAAG   3060
TTGATACATT AGGGACTTGA AGTTCAGAGT ATTATTAAAT CATTTCCAAC AAATATATAT   3120
AAACAGCGTC TTCCGGGCAG GTCAGGGCTT AGCTCAAGTC ACTTTCAGTT GCTGTGCCTC   3180
AGGGAGGATG CTGGTTAGAC CTCCCACTGA AAGATTTCCA TTGTTCTTCT AACTTTTCTA   3240
GCCAAACATG ATTCCAGTTA ATGTAACAAT CTCATAGCCT GGAAAGAAAC TGCCAGCCTG   3300
GGAAATCTAC TTTTCTGGCC TGGGAAGTAT TCTGGTGAGC ACTGAGGGAA GGGAGTAGGG   3360
GTGTTGGAAA GAAGACTTGA AATTCCTTTG TGTTATCTGT AAATAGAACG TTCTAACTCT   3420
TTGGTCTCTT CTTCCTCCTC TCCCCCAACC CCCTCTTTCA TCATTTTCAA TTATATATAG   3480
GAGGTTGGAA AGTTTCTCTT GAGCTCTTAA CCCCAGTCAC CTAAATACCC TTTGTGAGGG   3540
AAACTGGGTA AGAACAATTA AAGTGGAAGG CTCTCCTACC CTGGTCTTGC TCTTCCCCAA   3600
TTCTCCTCTA GCTCCTCCTC CCTTTATCTC TCTCTCTTCT CATAAAAGTG CTTTAGTTGA   3660
GGCTTCCTAG GATTCACCCT CCAGCTCCTA TCTGCACTTG AAGCCAGGCT GGGGTCTGCA   3720
CTTGCAATTA GTATGTCTGT TGGACTGGGC CACGGTATCC CACCTGGCCA CTGCCGCATG   3780
CCTCCTCAGT GCATGCCGGG GCTCCTGGTC TCTCTAGCCT GGGGCTTTGG GCTGACAAGT   3840
CCCCTCTTCC TTGCAGCTCC CTCAAAGTCC CAGACACAAA GGCCTCCAGG ATGCTCTGTT   3900
AATGCTTGAC TGGAGCCTTC CAAGATTAGA ATCAAAGGGG CATTTGGGGG TAGTTTTGGT   3960
CTTTGAGACT TCAGTCATCC CATATTCCCT CTACCCAATA GAAAGCAGAA GGGGCCTATA   4020
CTCTCATCTA GCAGCTTCTA GTTCCTCCTA TTTATTGGCC TTTTCCCTTG GCCCAGGGCC   4080
```

| | | | | | | |
|---|---|---|---|---|---|---|
| AAGGCCAGAT | TTTCATGAAT | AGGAAAGCTC | TCCTGCAGAG | AGATGTCAAA | CATGCCCAGC | 4140 |
| TAGACAATGG | CCATGAGCAA | CAAAAGATCT | GTGGGTGATC | CTGTAGGAGT | TTGATTCCCC | 4200 |
| CAGGCTGCTG | TGGGCAGGGC | TGTGTGGGTC | TTTAGATTGT | GTTGAGCAAT | GGTGGGTCT | 4260 |
| AGGAAGCTTG | ATTTCTGGA | GTTCAGTGAC | CTTGAATCTC | AAGTTCTCTG | TTTAGTCTTT | 4320 |
| CACTCTCGTG | AATGGGTTCA | GGTCTGAAGG | CCTGTAATTT | TTGGGTGCTG | AGCCCCGAGT | 4380 |
| TCTGAGCTGA | GAGTATCTAA | GCTGAGAAGA | GCACGGGTC | ACAGCCTTGG | TAAGTCAGAG | 4440 |
| GCACAGTTCA | GCCTCTGTTG | GCCCTTGGAG | CCAGCAGTTA | GTTGTCCTCC | CCAGATAGTT | 4500 |
| AATCGTGTTT | GTGGTTTTCC | CCCTTTAATG | GGCCGTGAAG | TCAGCAAACT | CCCCACATGG | 4560 |
| TGGCTCCCTT | TACTAAAGTT | GAGTAGTGAA | TTGTACAAGG | AGTCTTGGAA | ATTTTCAAAT | 4620 |
| ATTTCTCCAG | ATTGAACTCA | ACTCAGAATT | CGTGTGGGAG | GAAAGAGTAA | GGATTTTAAT | 4680 |
| GGGGTTCACC | TTTGACGTGA | AGCAAGGCGG | AAGACAGGAA | AGCCACAGTG | GGAATAGCT | 4740 |
| TTGGGCGCTT | TAGTAAGAAA | GACATCTCTG | CTTGATTATC | TGGTAGTGTT | CACCGCAGGC | 4800 |
| TCTTTGTGTG | CGAGCTTGCT | GCAGAGGCAG | AGCTGAACAC | GGAAAACACG | CATGTAAACA | 4860 |
| GTCCAACATA | AATCAGTGAG | CATATGTATC | AGAGAAAAG | AGACATATTC | CCATGTAGAT | 4920 |
| GTGGTTTGAA | GCTTTATTGA | AGGCAGACAA | TCTGAAGCAC | GGCCAGGAAT | AAACTAAGAG | 4980 |
| GAAGCAGACA | GTTTCGGTC | ATTCATGGCC | AGGAATAAAC | AAAACTTAGT | TTTTTTTTA | 5040 |
| AGAAGGAGGA | AGTATTAAAT | CTCAAATAAG | AGCAGGAACA | GCATTTAGAA | GGAGAAATAT | 5100 |
| AATATCTTGG | AAAAGCAAG | CAGAACTAAT | ATAGCTTATT | TAAATGTGAG | ATCCAAATCG | 5160 |
| TAGTAACAGG | AAACCCTCCC | ACTAAACTGG | AATTTCCCCT | AATTTTGTG | TAAGATCCAA | 5220 |
| ATAATTAAAA | TGCACTCTAA | TGGTTATTGA | TGGCTCTATT | TTCTTTCTTT | CTTTCTTCTT | 5280 |
| CTTCTTTTTT | TTTTTTTAA | AGAAATAGAC | CTGAGTTCTC | TTACTGGAGT | AGAAATATAT | 5340 |
| GAACCTTCTT | CAATTACCCA | GGAAATTGGA | AGCCTCTGGG | TGGATATGGT | CTTCCCTTAT | 5400 |
| TGCTTTCCTC | TTCCCACATC | ATTTCAGTT | AAAAAAATTA | ACTGTTTCCA | GCAGAGGGAT | 5460 |
| TCCTGTTAGA | AACCTTCATC | AGGTGAACTT | GTACTGGGAA | CCCTCATGCT | TTCCCAGTCT | 5520 |
| GTCTGTGTCT | CCCAAACAGA | GCTGAAGTTG | TAAACAAAGT | GGAAAAACAT | ATTTCTCACC | 5580 |
| CCAAAATTCT | TAAAATTTCA | CTTCTTGTGG | AAAACACAAT | TTCACAACAT | CAATTTTTAA | 5640 |
| AATCTGTAAG | AGCCACAGAA | GGTGTGAAAG | TAGCCAAACA | GCCGGTCTAG | AAATCCAAAA | 5700 |
| GCCAGGACTA | ACGGGGGACA | GAATGCTTTT | TCCTCAAATC | CAGGCAGGGA | TGGGGAGCAT | 5760 |
| TCTCAGCATT | AGGGCATTTA | TGGACGCTAC | AAGGGGAAAG | GATGTATCTG | AACGGTGGGG | 5820 |
| GTGATTTAGC | GATGAATCGC | CACGTTAATA | GCACTACTGC | CAAATCTTCA | AATTTAGAGG | 5880 |
| CTCTGGTGAA | AAATTAAACC | GGTGGCAATT | TTCAACGTTT | GTAGCATCTG | TTACCCTACA | 5940 |
| CTTCAGCACC | CGGAGTCTGG | ACAGCTCCGC | AGGCCGCGCT | CCGGAGGCAG | CATGAGCTCT | 6000 |
| CATCAATCTA | CTCATAGCCC | TACTGTCAAC | GGCAGCCAGA | CTCAGGAGAG | ATTACTGAA | 6060 |
| AATCCTCCAA | GACTTCCCTT | TAAAAACAAA | ACGACTTCCA | CATTTAATGG | TCTATCTGAA | 6120 |
| AGAACATACG | CAAGAAATTA | GGAGATCTAA | ATTAAATTTA | TTAATAGGAG | AGCTTGATGA | 6180 |
| TGCTTAATTC | CAGAGACCAG | AGCTCCGATT | GGTGAGGCTT | GATGAAAAAG | TAAAGAGAAA | 6240 |
| TCGTAATTGT | ATAGTTAAAA | ACATAACTTT | TGTCATCCTC | AAAATTCTAA | AAATTCTTTA | 6300 |
| CCTGTCCTTG | GGAAATGGGT | GAAATTGAAA | ACCATCAAAA | CAATTGGACT | TCTTAAAAAT | 6360 |
| TGGATTGTAT | GAGTGAAAGG | TGTTTATGAG | AAGTCGATGA | CTCCGGATCT | TATCATCCAA | 6420 |
| GAGGACAGCA | CAGAATAGTT | AATATGTTCC | TTGAGGGACT | AGGATGCTGA | CGTCTTTTTC | 6480 |

| | | | | | |
|---|---|---|---|---|---|
| TGATACCCGA | TCATTACGTG | ACTGAGAAAA | AAAAAAAGGA | AGTCATTTCA | TGAATAAAAA | 6540
| TCGGAGCGCA | ACAGTGCAAC | AAAATATTCT | GTACTTAAAG | GCAACAGGCA | GGCAGATGTT | 6600
| GACAAAGAGG | GCTCTCCAAA | AACCATGTTC | GGATAGATTT | TTGCGAACTG | CACAGATAAA | 6660
| TAGGAGCAGA | AGGCCGGTCA | CCTCTGTAAC | CAGCGGTAGC | AGCAGCAGAA | GCCGCAGCTT | 6720
| CAGAGGCAGC | CGGAGAGACC | TCGGAGCAGA | GAAGGCGCCG | CCGACCCTCG | CGGCTGCCTG | 6780
| GCCCGCGGCT | CCTACAAAGG | CGGGCTAGCC | GCCCGCCCTC | TCCCTTGCCT | TCCTCCCCTT | 6840
| CTTTTCTGAC | TTTCCCTCTT | TCCCTTAATC | GCCTGCTTCT | TCCTCCGGGT | GGACTTACGG | 6900
| CCACCTTGCT | CCTCCGCGCT | TCACCTCATC | GCCCCCTCTT | TCTTTCTTCT | GCCTCTCTCT | 6960
| CTGCGCCCCC | TTCTCTCCGT | GTCACGCTCC | CTCCTGGTTC | TGCGCGTCTA | CAAACTTTTG | 7020
| AGCAGAACAC | GAGCCTCGGC | AAACGAGTCC | CGCAGCTCCT | CCTGCTGCTC | CCGCTGGTTC | 7080
| CTGCGGCTTC | TGCTCAGACA | CCAACGCCAG | ACGGCGATGC | CTCTCGGGTG | GTGACTCCAG | 7140
| CGCAGGAACT | TGAAGAAGCG | CTTTGCCCGC | CGTCCTACCT | GGCAGCTCTC | CTGGCAGCGG | 7200
| GAGGAGTTGA | AGGGTAAGGG | AGGGAAAATC | TTACCAAAGC | GACCGGCTCA | CTCGACTGCT | 7260
| GATTCTTTCG | CTTGGCGTCG | CGTCAGGGGA | GTTAGCTTTC | CTTCAGCCGG | GTCTGGCTAG | 7320
| TTATTGGGCG | CCGGGTAGAT | GCATATATAT | ATATTTTTTT | CTAACTATAG | CAAGCAAGAA | 7380
| GTGGCAGGGC | GCGCACCGGC | TGTCGCCAAG | TGCTGTTCAA | CTCAGGGAGC | CGGGGCTTCG | 7440
| CTCCGTCCCT | CCCCCGGCTT | CCAGAGCTTT | TTGGGGTTGG | AGGGTGGGAG | GCCAGGGGCG | 7500
| TTCTCACAGC | TGTGTGTCCT | CTTTCCCATC | CTGCGCAGA | ATG ACC ATG TGT AGC | | 7554

```
                                                    Met Thr Met Cys Ser
                                                     1               5

GGA GCG AGG CTG GCC CTG CTG GTC TAT GGG ATA ATC ATG CAC AGC AGC        7602
Gly Ala Arg Leu Ala Leu Leu Val Tyr Gly Ile Ile Met His Ser Ser
         10                  15                  20

GTC TAC AGC TCA CCT GCC GCC GCC GGA CTC CGG TTC CCC GGG ATC AGG        7650
Val Tyr Ser Ser Pro Ala Ala Ala Gly Leu Arg Phe Pro Gly Ile Arg
     25                  30                  35
```

| | | | | | |
|---|---|---|---|---|---|
| TAGGTGCTGG | CTGCCTGGCC | CAAGCAGGAG | CTGGGCTCC | CCAGGCACAG | ACGCTTCCTC | 7710
| ACGGTCTCCT | TCCTGCAGTC | CTTTGGGTCC | AGACTACTAG | CATCGCCCTC | TGCGCCCCG | 7770
| GTGCGCCTCC | GCCAGCCTCG | GCTGGACAGC | GGGTCCCCAT | TCTAGCCGAG | GGTCTGGCAG | 7830
| GCTCCGCGAC | TGCTCGGACG | CCTCCCCCAG | CCCTAGGCAG | CTCAGGGTCC | CGGGTAGAGC | 7890
| CAGTGAGCTT | CTGGCCGCTG | GAGAACCCCC | CCTCCCCCAA | CCCGGCCCAC | AGGATGGGGG | 7950
| CAGGGCACGG | CCCCTAGCTT | GGTTTCTTTT | ACCTATTCTT | GGGACGAGTT | AGGAGAACTT | 8010
| CAGCTCTGGA | GCCTGGCCGG | GGGTTGAGCG | TGAAGCTCCC | TCGGACTTTG | CTTTGTTACT | 8070
| GCTTGTTCTG | GACTATCCGG | GTGGGGTCTC | TCTCTCTCCT | CCACCCTTTC | TTTTCATTTC | 8130
| ATTCCAATTC | TTTCCCCTGA | AGAGCTTTCT | TTCAAGTGAT | CCGTGTTCCA | ACTGCATTTT | 8190
| GAATCCCAGG | CTGTCTTGGG | GGGCGTGCGG | TGGGGAGGGT | GTTGGCCCGG | TGTGATTGAG | 8250
| GAAAGCGAC | TTAAGAGAGG | GAAGAACAAG | GACGAGACTG | CGAAGGAGGG | GGAAAAACAG | 8310
| GCGCAAAGGA | GGAGGAAGGG | AAAGCCAGCA | GGCAGGCAGG | ACCGGGAGAG | CAGCCTGCC | 8370
| TGGCCCGGGA | TGGAGGAACC | TTGGCTTTTT | TCTTAACCCC | GGGTTTCTAA | CCCGCAGGCG | 8430
| CGGCCCAGGT | TCCCGGAGGC | AGCCCCAGAG | TCGCGGGCCG | ATGTGCCAGG | CTGTGGATGA | 8490
| GCCCCGGGTA | GGGGAGGGTT | CGTACCAGCG | GCGCCTGGGG | CAGCGAGGAG | CGCGCGTTCT | 8550
| GCCTGCGAAG | CTGCCTTCTC | CGAGCCCCGC | CCAGGAACAT | TAGCTCTGGG | GGGCCGCTGA | 8610

```
                                                        -continued
TCATTGATTT  GGACGGAGAG  ATGGGTTCTG  GGTTCTGTAT  TAGGATTCCA  GCATCTGGGC   8670
TCGAGGCAGG  GCAATATCCA  GAAAGACCCC  AGGGTTCGGG  GTACCCGGGC  CAGGGCTGAG   8730
GCGCATCGCC  GAGCAAAGGC  TGGGTGCGAG  GCGTGCGGAA  TGATGCGCTT  GCCTTGCCCG   8790
GGCCTCTCCA  AGGATGGAGA  AAAGGCGAGT  GAAGTAGCGA  AGTACGACTC  CAACCCCGCC   8850
CAGAGAGTGC  TACTAGCGCT  GGCTGCACGC  CAAGTCTCTC  CAGGGGTCCA  AAGCGAGAGG   8910
GATTTGTTTT  AACCCATCTC  TACCCGTCCT  GTGTCAAGAA  CGGAGGCTGT  AGAGGCGAC    8970
TGCGAAGTCG  CCAGGCACTC  GCTGGATCTC  GGTCCCCCTC  CTCGTGCTCT  GGGGTTGAGA   9030
TGGGGCACCG  CCATCGATAA  CAGATCAGCG  CGAACTATTC  GTTAGTGGC   CTTAAAACAC   9090
CCTGGTTTCA  CCCTCAGCTA  TTTTCAAGTT  CCCGTGTGCC  TGGCACTTTC  TCCGTGCGAG   9150
AAGCACCGGA  GGGTGCGGAC  GCGCCACAGT  CTGAGCCGCC  GCCGAACTGG  CTAAGTTTAG   9210
GGGCATTTAT  TATTCATGTT  CCTGCCAGAT  CCTCGCCTGC  CCAAAATAGA  AACCGAGGTT   9270
CTCCGTGACC  TACATCTGCT  CGGGGAAGGG  CTCCCCTGGG  CTCGGAGGCT  GGGGTGGGGG   9330
TGGCTGAGGA  GTTGGCCCCC  GCACGCCCCA  CGCATCCTCT  CCTTTGCTTT  CTGGGCCTCC   9390
CCATTCGGGT  CTTCGCGTGG  GTCAGCGCCC  GGTCTCCCAG  GGCCTTTCTC  GTCCCCGCCC   9450
GTTGCTGCTT  TGGGGAGGCT  CGGGAGCCAG  GCGGGGAGGG  GGCGGTCCT   TTTCCGTAGA   9510
CAGGTGTGCG  CGATCGGCGG  AGACGCCTCG  GTTTCCCAGC  GCTTGTTGAG  GCCGTGGCCC   9570
GCAGGACGAC  CCTTTACCCG  CGAAGGGGGG  GTGGGCGGGA  CCGCCGGCG   GGTAGGAGT    9630
GGTTGGGTGT  CGTTGCCTCC  TCCTTACCTC  TGCTCCCACC  CCCAGTCCTG  GGAGAAGAGA   9690
CAATTCTCAG  CGGAGGACTT  TTATCACCTG  TGAAAATCCG  CGCGAGCCCC  TTACTTTGGA   9750
TCCTCGCCGA  GCTGGGGAGG  AACTTGCACT  GACCACACCT  TCTGTCCCCG  GCCACCCCGC   9810

AGG CCA GAG GAA GAG GCG TAC GGC GAG GAC GGA AAC CCG CTG CCA GAC        9858
    Pro Glu Glu Glu Ala Tyr Gly Glu Asp Gly Asn Pro Leu Pro Asp
        40                  45                      50

TTC GGT GGC TCG GAG CCG CCG GGC GCA GGG AGC CCC GCC TCC GCG CCG        9906
Phe Gly Gly Ser Glu Pro Pro Gly Ala Gly Ser Pro Ala Ser Ala Pro
        55                  60                      65

CGC GCC GCC GCC GCC TGG TAC CGC CCG GCC GGG AGA AGG TGAGATTCGC         9955
Arg Ala Ala Ala Ala Trp Tyr Arg Pro Ala Gly Arg Arg
        70                  75              80

GCGGCCTCGC GCACACCCGC GGCTGGGAGC TCGGGACTGC GGTGACGGGA GGGGCAGTGT      10015
GGTGACCCAC CCAGGATTTT TTTTTTTTTT CCCGTGAAAG TCCTCAAGCC TGTCCTCTCC      10075
CTGGCCCGAT CCTATTGCAG CGACAGAAAA TCAGCAGCGG GCGGGTCTGT GTGGACCTGA      10135
GGGCCGCGTG GGGACCGAGG GGGGCTGTGG CCCAAAGAGT GGCAGTGAGT GGCGTCAAGG      10195
AACCCACACT CCGCATCTGC CACTCCTAGA GCCGGGACTA GCTCCCGATC CTAGCAGTTG      10255
CTCTCGAGAT CATCCCGGGA GTTATTGGCG AGTTCTGGGC CTCTGGAGGT TTCCCTGTCA      10315
GCCTCCCCGG CCGCCGAGGG GGCGCGCGCC CAACAAGGGG GTCTCTAGCG GCCACCTGGG      10375
GACAGAAACA GTGACCCTGG GCGCGCACTT TGCCTCCCCG TTAGA GAT GTC GCC          10429
                                               Asp Val Ala

CAC GGG ATC CTT AAC GAG GCC TAC CGC AAA GTG CTG GAC CAG CTG TCC       10477
His Gly Ile Leu Asn Glu Ala Tyr Arg Lys Val Leu Asp Gln Leu Ser
 85              90                  95                      100

GCC GGG AAG CAC CTG CAG TCG CTC GTG GCC CGG GGC GTG GGG               10519
Ala Gly Lys His Leu Gln Ser Leu Val Ala Arg Gly Val Gly
            105                 110

TAAGAGTTTG TGGAAGGATT AACCTGCGCG CGCCGGGGTG GGTGCCTGTG CGGGGCGCGC      10579
GGGGCGGGCG GCGGTGGGTG CCCGTGGGGG CCAGGGTGAG TCTGCGCCCC TGGGTCTGGG      10639
```

| | | | | | | |
|---|---|---|---|---|---|---|
| GTGGGCATCC | GCCACGGGTC | GCAGTTGGAG | ATTTTGAAGT | GGCACTTTAA | ATTTGCCCAG | 10699 |
| AGAGCTCTGG | AAGAGGCAAA | AAGGGAACGC | GAGCCAGGGA | GTTTGATCCG | TTTTGAATGA | 10759 |
| AAAGAAAGAG | AAACCAAACC | AAACCTCTCA | GTCATCCAAA | ACCTTCAGGC | TTCCAGGGAG | 10819 |
| GTTTTGCTAT | AATTTTCTCT | AAGCATGACT | GTTTCTGGGG | GAGGGGAAAG | GGGTGGTTGT | 10879 |
| ATTTACTGAA | AATTCAAATC | GAAATAATAA | ATGGCCAAAT | GTGGACACTT | ATGGACCCAA | 10939 |
| ACAGTTTTGC | TCACGCCAGA | GAAACTGAGA | GCACAGGGCT | TGCGTGAAGC | CTATCTCGGC | 10999 |
| AGAAGGCAAC | ATTCTAATAA | AGCCCGTGGG | AAAACAGATT | ACATTTCGC | CATGAATAAG | 11059 |
| TCATGCAGTG | AAAAATATTG | CCTACAGCCT | GTCGACTTAT | ATTATTATCA | CGTTTTTCAA | 11119 |
| CTCGGCGTGA | GGAGGGAGAG | GAGTGTTCAT | ATTTGACTAG | GAATTGCAGG | ATCGATGCAA | 11179 |
| ACTCCAGGGC | AGCAGCCAGA | CTGGCATATG | TAGGGCTCTC | CGGTTACTTT | CTCTGTATGT | 11239 |
| CGCGGGTGAG | AGGAACAGCG | AGGACAATTT | AGCGCAAACA | CACGAAGGGT | CGGATCTCAA | 11299 |
| GGGGGCAGCG | CTGGGAGAAA | GGTTAGGCTT | GAAGCGCGCG | TCGCCTGCCC | GGATCTTATC | 11359 |
| CCGGGCCCCC | TCCGCAGGGT | TTGGTGCCAG | GAGATCCTGC | GTGGGGAGGG | GGGCATCGAG | 11419 |
| GGGCTGCCGT | CTCGGCCCTC | CCCACGGCTG | CTTCCAGGCA | GAGGCGGGCG | ACGCGGTGGG | 11479 |
| CAGTGCGAGC | CCCGGGCCCT | CCCCGAAGGC | TCCCGCGTGG | GGTGGGGCCC | GCCTGCTCCC | 11539 |
| CGCGGCGATT | GAACCTGTGT | CTCCCGCCCC | GCCACCCTCT | TCCCGACCCC | TTTGCTTGCA | 11599 |

```
      GT GGG AGC CTC GGC GGC GGC GCG GGG GAC GAC GCG GAG CCG CTC TCC                              11646
         Gly Ser Leu Gly Gly Gly Ala Gly Asp Asp Ala Glu Pro Leu Ser
         115             120                     125

AAG CGC CAC TCG GAC GGG ATC TTC ACG GAC AGC TAC AGC CGC TAC CGG                              11694
      Lys Arg His Ser Asp Gly Ile Phe Thr Asp Ser Tyr Ser Arg Tyr Arg
      130                 135                     140                 145

AAA CAA ATG GCT GTC AAG AAA TAC TTG GCG GCC GTC CTA GGG AAG AGG                              11742
      Lys Gln Met Ala Val Lys Lys Tyr Leu Ala Ala Val Leu Gly Lys Arg
                          150                     155                 160

TAT AAA CAA AGG GTT AAA AAC AAA GGA CGC CGA ATA GCT TAT TTG                                  11787
      Tyr Lys Gln Arg Val Lys Asn Lys Gly Arg Arg Ile Ala Tyr Leu
              165                     170                 175
```

| | | | | | | |
|---|---|---|---|---|---|---|
| TAGCGATGGG | TTACCAGCTA | CCCTGTGTAT | ACAGCCCTGA | CGCAATGAAA | AGTCGTTTTC | 11847 |
| CAAACTGACT | CAACAGTCAT | CGCTCGTGTG | TTCTATCCAA | ACATGTATTT | ATGTAATGAA | 11907 |
| GTAAAGCCAT | TAAATGAATA | TTTTGATAAT | AATATTGTTT | TTCTTTCTAC | AAAGCACTAG | 11967 |
| AGAATGCACA | GATATACTTT | GTGGACCAAT | TATTGATATA | TATTATAAAT | ATATATAAAG | 12027 |
| AATATATATA | TATATATATA | TATAAAGTAT | AGAGAGAAGT | TCATACAAAG | CGTGCACAAG | 12087 |
| GATTGAAAAT | TCGCCCGAGC | TGTTTATGTT | TTTATAAAAA | TAAATAGAAA | AGTAGACAAT | 12147 |
| CATTGTTTTG | AATATTACTC | CTATTTTTGT | AAACTGGAAT | TAAAAGGATA | GTATTTTTAT | 12207 |
| CCATGACAGG | CCTGAAGATA | TTACTACTTA | CCATTTGCTA | CTGTACATAA | ACAATGATGC | 12267 |
| CCTGCTCCAG | GGAGATTTTG | AGGTAAAGAT | ATGGAGAATT | GCTGAAGGC | ATTCTTTCCC | 12327 |
| AGTGAGTCTC | TGGGGCAGGC | TGCTTCAATC | CCAGCCTAAC | TCAACTGGGC | TCTGTCCCCC | 12387 |
| TGGTTGGGTG | GCAATTCCAA | TATTTCTGCT | TTCTTTGATT | CTCCTTTTAT | GTGTAGTTGT | 12447 |
| CTCTCTTCAG | ACTCTCAGCC | CAGAAGAAAA | TTCTCCTGAT | AAAACAACAG | CTCGATCCAA | 12507 |
| ATTGTGCTTC | TCCCCAGAAT | TCACGCCTCT | CCCTAGGAGA | AGAGTTGAGG | AACTGTACAG | 12567 |
| AAAAGGGCGG | CTTCGTTAGA | CCGCTCTCTT | TTCTGTACTT | CCTGAGTGGC | CAGGGAATCT | 12627 |
| AATATCCCCA | AATTAGGGCA | ATTGGAACAA | AGTGAAGGAC | ATAGAGGTAT | ATTGGAAGAG | 12687 |
| GCAGAGCCTG | AGGTGGTAGG | AGGACGACCC | TGGAAATGGA | CTGGTTTGAG | ATTGCCCCAG | 12747 |

```
GTCTGGGAAG CTGAGGGCAA ATCCAGTCCC AGTGGTCCTG ACTTTGGGCG CTGGGTATTG    12807
GAAATGGATG CAAAGTACAA TGTGTTTTTC TCCAGTGCTG TCCATGCTTC TCATCTTGTG    12867
AAATGGCCAG GATCCTCTCC TTTGAAACCT GCTCTGTAGG AGCTACCCTT TTCCTTTGTG    12927
GTTTTATGGA GACCTCTCCT TCCTACCCTC CTGCACTGTT TAAGTACTGT TTACCATTTT    12987
TCATTCACTT CTCTTAAACT TGTGAATGCT TCTCACTTTT TTTTTGTTT GATGCAGGCA     13047
CTTATTGTAA ATTTTAGAAA CCCCTCTGTA GCCACTAGTA AGTAATTATG CACTAAATAT    13107
GAACCCTTTG TTTCTTGTTT ATTGAGTTTG TAGGTAAAAT GTATTTTCT ACATTATTGC     13167
TTATTGCTTA GTAAAATTTA TTTCATAAAA CCAACCTTTG TCATATTAGA ATGTGTAGTG    13227
TTCACATGTT GCTCAGTTTT GCTAACTGAT AAATCATTTA ATCCTCTTCT TCATATGTAT    13287
GAGTACTATC TTATATCTGT GGTCAAGAGT GAGGTAAGCA AGCTCCAACA GACCCTGAGA    13347
ACCTACGCTT GTATCCTTTC TTTGGCTAAA GAAAGCATGT CTGTTTCCTG TCAATTCTTT    13407
GAACATACAG AGTAATCTTT ATAAACAAAA GAACCTTCAC CCAGCAATCA GATCGAGCAG    13467
CAACAGACAA ACCAGCCAGC CAATCTCCCA AATTTCAGGC ACAAGTTTAT TTTTTTTTT    13527
TTTATGTTTT GAAAAAGAA GATGAAGAAG AAGAAAAAAA AAGAACAAG GAAAGATTAA     13587
ACGTTAGCTT GTAAAGTTTA AGGACCTTT CCTTTTCCTT TACGGATTTG ATCAGTATGA    13647
AGTCATAAAT CAAAGAAAAC AGAATTGGAT TTGCATTCCC AGGCGGGATG GATGCTGCCA    13707
GGAGATCACA TTGCAAATAG TGAAAACAGA GGCATTCGGT CTATGCCTGA GTCCTGTGTA    13767
TAGGATCAAT CTTCCTTTAA TTCCGCAGTC TCCTCAGGCA ATGTGACACG GATGCAGTT    13827
TGCAGCTTTA GTGCCTTTCT TCGCCTTTTA AATTGCCACG AATCACAGAT GGCTATTTAG    13887
TGGCCCTACA ATGCTGCAAC ACATCAGCTT GCATTTTAGT CTTAATTATT TGTTTCTTGG    13947
ATAATGGGCA GAGTTTTCTG TATTTGTATC GACTGTTAGT GGTGAAATAG GGCTCTAGTT    14007
AACCTTTTAT TTATGAAGTC TAATTTAGTG TTCCCGTGGC TAGTTGCAAG CATTTTACAG    14067
TGATCACCCA GTTAATCTT TTGTATACTT TTTAGAAATG CCAAGAGCCT TACTAAACTG    14127
AAGCAGATTT ATGATATAGT GATAATTTAG GTAGATGTTA GTCTTGAAGC TCTTATTTTG    14187
TGTGCAACTG ATTATAAAAA CACCTTAACC AAGTATTATT ACACACATGA TATCTATAAC    14247
TAGGACTTTG ATAACTGTTA TATAAAGTGT GTAAAATTTG TATGAATAAA TTTTTGTAAA    14307
CAATGCAACT TGGTCTAATG TTTGGGAAAA AAGACATTCA GGAAATAATT ACTTTAAAAT    14367
CTCTTAAAGT ATTATATTTC TTTAGCAACC ATAAGATTTT TTTACGTCTG GAATATATAT    14427
CTATCTAAGC ACCCTTGTAT TTTCATGAAC TGCACTTTAA TAATTGATGG GCAACTGGAT    14487
TCTGCTAAAA ATTTAAAGTA GCTACTCAGA TGGAGATGCC TAAGAAGGTT TTAAGCTCAT    14547
AAACAGGCAT GATGTTGCAA CATTATAAGA CACACAATTT AGATTAATTT CCATCCCCTA    14607
GTGTGTATAT ACTTTGCTCA ATATTCAGAA AGTTACTAGG TAGTAGTGGG AGACAATGCT    14667
GGAGCATTAG TTACACATCT AAAATAGCAA TCTAACATTG TTCTTTTATT TTTTATTTTA    14727
GTGGCCAGGT CTCACTATGT TGCCCAGGCT GGTCTTGCTC AAGCGATCCT CCCACCTCAG    14787
CCTCCCAAAG TGCTGGGATT ACAGGCGTGA GCCACCACAC CCAGCCTAAA ATAGGGATCT    14847
AACATTGTTC TTATACAAGT AACTCTGCAG ACTAAACTTG TCTTGATAAA ATTTTGTATA    14907
AAATGATCTA AATAATCAGT TTTTGGAGGT TTTAAAATGT ATTTAGAGAC ATACAAACTA    14967
CTGTCTCTGA TTAAAATGCT TTAGGTAGAA GGAACGTGAA CATGAGTAAG TAAAGAGTTA    15027
ATTAGATGCC TTTAAAAGAA AATGTACTTT GAAGTCCAGG AAGAAACACA AGAAGTCATT    15087
TGTGGATTGT ATGCTTTCTT AGTTCATATT TACAAACTTT AGGGCAAAGC TTTCATACGA    15147
```

| | | | | | |
|---|---|---|---|---|---|
| AATTCCTTCA | AATTCCGTAG | TGGTGTGTGT | TTTGGCACCT | TGACTATTT | CTGGCTTAGA | 15207
| AAATGTATAG | AAAGTCACAC | AATAATTGAC | ATACCATTTA | ATTTAAAATG | CCAGGGTTTC | 15267
| ATCCTAAAAA | TTAATGGTCT | CAATTAGTAA | ATCAATAAAT | ATGTTACGAT | AGAATTAAAG | 15327
| GATGAGTGAG | GATTCTAAAA | TTATCTTCAG | AATTTAGCTC | AGTATTTAAG | GCCTAGAATC | 15387
| AAATAGGGAG | GAGCCCACAG | TCTAGAAATC | CCGTTTGTAG | TCAATGAAAA | AATGAATCCA | 15447
| GTACAGTTCA | TATTTGCATT | TGATTTTATT | GGATAAGGAA | TTTTTCTTCT | CCATCTTTAA | 15507
| CTGCCCCTCT | TTGTCCTTGA | AGACATAGTG | TGGTAGATGA | AAAAATGAAG | AAGACTTTAT | 15567
| TCGGTTGGGG | CTAGGCTAAT | GACTTGTCAA | GAACATAAAG | ATAAACCCCA | GACTTGGCTG | 15627
| ACTTCAAGTG | AATTTCATGT | ATTTAGCAAC | TTGCCATATT | ATCTTCGGTG | ATAACTCAAA | 15687
| TTACATCTTT | TTAAAGGCAG | ACTTGATACA | TATGGGTATT | CAAGAAGCTG | TAATAGGTGC | 15747
| CTTAATGCTG | TTAGGGCGGA | GAACACACTT | ATTCAATACA | ATGCACACTT | ATTGAACACA | 15807
| TGAAATGGGC | CACCGCACTG | GTCGAGAGAG | CTTGACTAAC | ACCTGGGAGC | TCAGGTAGTA | 15867
| TTTTTTTCAG | AATGTTTTC | TGAAATGTGA | TCATCTTTGG | GGCGGGGGGA | GCTTAAAAAT | 15927
| GCAAAATTGT | AGGGCTCTGC | CAGATCCAGT | GAATCTGCAT | TTTAAATAAA | AACCCTAGAT | 15987
| TACTGTGCAC | TAAAATTTGA | GACTGCCTAG | ATTTAGAATT | GGTGACATAT | GTAGGCATAC | 16047
| ATATGTGCTG | GTCTGAATGT | TTTTTTCATA | TGAAATAAGC | AAAAGGTCAT | GTTACCTGCA | 16107
| TACAGTAATA | AATACATAAC | TGTGCCATAT | TCTTCCAAGA | TATCTGGTCA | TTAAGCTCTT | 16167
| TGACAATTTC | AGTATTTCCT | TTAGGTCACT | AAAACTACTA | GTTAGCATTA | TTTTACTTGT | 16227
| ACAGTCTGGT | TGGACCTCTC | CTACAGGAGC | TTGTGGAAGG | AGAGTGATCC | TCTAAGTTGG | 16287
| GTCCAAAATA | TTCAATCACA | GGACTAAGAG | ATTATGGCTA | TAATGAGGAG | AACTTGTGCA | 16347
| GCTAGCTAGC | CATAATTCTG | GGGATCCAGA | AGTCAACTTC | CAGTTGCATT | ATATCCCAAT | 16407
| TTGGTTTGAA | TGTATTTACT | GCTCCCCAAC | TGTTTACATG | ATGGTTTCTC | TTGGATGGCT | 16467
| CACTATGACC | TTCAACCCAA | CCCTACTGTT | CACATGATCA | CAAGATTGGA | AGCCAAGATC | 16527
| AAGTCATCCC | TCTTCTCTTT | TGTTGCCACT | CTTTTTTGTA | GAAGGGAGAT | GCCAGCTGCC | 16587
| CCTGCTGCTG | CAGATTGCAT | CACTGCTGGA | TTCTTACATT | GGTTTGTAGT | TGGTCATCCT | 16647
| GGTCACTTCC | CCTGCAACCA | CATAGTTTTA | GCTCCATCTT | AGTATCATGT | CCCTCTGATC | 16707
| AGATGTTCCA | GAGTAGCTTC | CATTGTCAAA | GGGTTAAAGG | GTTAAGGTA | ATCAGTAGTC | 16767
| AATTTTACCT | CTCTGTTCTT | CAACACGATC | CTTCCTCTTT | TTTTGTTTT | GAGAAAGGGT | 16827
| CTTACTCTGT | TGCCCAGGCT | GGAGTGCAGT | GGCACGATCT | CGGCTCACTG | CAACCTCTGC | 16887
| CTCCCGGGTT | TAAGCGATTC | TCCTGTCTCA | ACCTCCCGAG | TAGCTGGGAT | TACAGGTGCA | 16947
| TGCCAACGCG | CCCGGCTAAT | TTTTGTATTT | TTAGTAGAGA | CGGGGTTTCA | CTGTGTTGGC | 17007
| CAGGCTGGTC | TTGGACTCTT | GTCCCCAAAT | GATC | | | 17041

( 2 ) INFORMATION FOR SEQ ID NO:2:

( i ) SEQUENCE CHARACTERISTICS:
        ( A ) LENGTH: 176 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Thr Met Cys Ser Gly Ala Arg Leu Ala Leu Leu Val Tyr Gly Ile
 1             5             10           15

| | | | | | | | | | | | | | | |
|---|---|---|---|---|---|---|---|---|---|---|---|---|---|---|
| Ile | Met | His | Ser | Ser | Val | Tyr | Ser | Ser | Pro | Ala | Ala | Ala | Gly | Leu | Arg |
| | | | 20 | | | | | 25 | | | | | 30 | | |
| Phe | Pro | Gly | Ile | Arg | Pro | Glu | Glu | Glu | Ala | Tyr | Gly | Glu | Asp | Gly | Asn |
| | | 35 | | | | | 40 | | | | | 45 | | | |
| Pro | Leu | Pro | Asp | Phe | Gly | Gly | Ser | Glu | Pro | Pro | Gly | Ala | Gly | Ser | Pro |
| | 50 | | | | | 55 | | | | | 60 | | | | |
| Ala | Ser | Ala | Pro | Arg | Ala | Ala | Ala | Ala | Trp | Tyr | Arg | Pro | Ala | Gly | Arg |
| 65 | | | | | 70 | | | | | 75 | | | | | 80 |
| Arg | Asp | Val | Ala | His | Gly | Ile | Leu | Asn | Glu | Ala | Tyr | Arg | Lys | Val | Leu |
| | | | | 85 | | | | | 90 | | | | | 95 | |
| Asp | Gln | Leu | Ser | Ala | Gly | Lys | His | Leu | Gln | Ser | Leu | Val | Ala | Arg | Gly |
| | | | 100 | | | | | 105 | | | | | 110 | | |
| Val | Gly | Gly | Ser | Leu | Gly | Gly | Gly | Ala | Gly | Asp | Asp | Ala | Glu | Pro | Leu |
| | | 115 | | | | | 120 | | | | | 125 | | | |
| Ser | Lys | Arg | His | Ser | Asp | Gly | Ile | Phe | Thr | Asp | Ser | Tyr | Ser | Arg | Tyr |
| | 130 | | | | | 135 | | | | | 140 | | | | |
| Arg | Lys | Gln | Met | Ala | Val | Lys | Lys | Tyr | Leu | Ala | Ala | Val | Leu | Gly | Lys |
| 145 | | | | | 150 | | | | | 155 | | | | | 160 |
| Arg | Tyr | Lys | Gln | Arg | Val | Lys | Asn | Lys | Gly | Arg | Arg | Ile | Ala | Tyr | Leu |
| | | | | 165 | | | | | 170 | | | | | 175 | |

( 2 ) INFORMATION FOR SEQ ID NO:3:

( i ) SEQUENCE CHARACTERISTICS:
        ( A ) LENGTH: 657 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
TGAGAAAAAA  AAAAGGAAG   TCATTTCATG  AATAAAAATC  GGAGCGCAAC  AGTGCAACAA    60
AATATTCTGT  ACTTAAAGGC  AACAGGCAGG  CAGATGTTGA  CAAAGAGGGC  TCTCCAAAAA   120
CCATGTTCGG  ATAGATTTTT  GCGAACTGCA  CAGATAAATA  GGAGCAGAAG  GCCGGTCACC   180
TCTGTAACCA  GCGGTAGCAG  CAGCAGAAGC  CGCAGCTTCA  GAGGCAGCCG  GAGAGACCTC   240
GGAGCAGAGA  AGGCGCCGCC  GACCCTCGCG  GCTGCCTGGC  CCGCGGCTCC  TACAAAGGCG   300
GGCTAGCCGC  CCGCCCTCTC  CCTTGCCTTC  CTCCCCTTCT  TTTCTGACTT  TCCCTCTTTC   360
CCTTAATCGC  CTGCTTCTTC  CTCCGGGTGG  ACTTACGGCC  ACCTTGCTCC  TCCGCGCTTC   420
ACCTCATCGC  CCCCTCTTTC  TTTCTTCTGC  CTCTCTCTCT  GCGCCCCTT   CTCTCCGTGT   480
CACGCTCCCT  CCTGGTTCTG  CGCGTCTACA  AACTTTTGAG  CAGAACACGA  GCCTCGGCAA   540
ACGAGTCCCG  CAGCTCCTCC  TGCTGCTCCC  GCTGGTTCCT  GCGGCTTCTG  CTCAGACACC   600
AACGCCAGAC  GGCGATGCCT  CTCGGGTGGT  GACTCCAGCG  CAGGAACTTG  AAGAAGC      657
```

GENOMIC DNA EXONS HAVING EXONS ENCODING HUMAN PITUITARY ADENYLATE CYCLASE ACTIVITY PEPTIDE WITH 38 AMINO ACIDS RESIDUES(PACAP38) AND A PROMOTER THEREOF

CROSS-REFERENCE TO RELATED APPLICATION

This application is a Continuation-In-Part of U.S. application Ser. No. 08/047,246, filed Apr. 13, 1993, now abandoned, which is a Continuation of U.S. application Ser. No. 07/741,676, filed Aug. 7, 1991, now abandoned.

FIELD OF THE INVENTION

The present invention relates to a genomic DNA of human pituitary adenylate cyclase activating polypeptide with 38 residues (PACAP38) which is a bioactive peptide derived from testes or brain hypothalami, a DNA containing a DNA sequence coding for the peptide, a promoter of human PACAP38, a vector containing the promoter, a vector containing a DNA coding for a structural gene of a peptide downstream from the promoter, a transformant bearing the vector, and a method for preparing a protein such as mature PACAP38 peptide using the transformant.

BACKGROUND OF THE INVENTION

Various hormones secreted by brain hypothalami and hypophyses are well known. Examples thereof include thyrotropin releasing hormone, luteinizing hormone releasing hormone, somatostatin, adrenocorticotropic hormone-(ACTH), growth hormone(GH) and prolactin. The action of these hormones has been well studied. A novel peptide consisting of 38 amino acid residues which has the adenylate cyclase activity was discovered in a different hormone derived from sheep hypophyses. The structure thereof was determined and the peptide was named "PACAP38" (EPA 0 404 652).

The present inventors filed a patent application (Japanese Patent Application No. 1-155791/1990) on cDNA of sheep PACAP38. Further, cDNA of human PACAP38 was cloned from the cDNA library of testes and the amino acid sequence thereof was also determined (Japanese Patent Application No. 1-259924/1990).

The amino acid sequence corresponding to human PACAP38 is the same as that of sheep PACAP38, although there is substitution of some amino acids in the precursors thereof.

In general, when an amino acid sequence such as a bioactive peptide is determined and cDNA is cloned, its expression mechanism can be studied to determine the physical conditions under which transcription and translation of the gene take place. Understanding the expression mechanism aids in the development of drugs for inducing the expression of the gene. PACAP38, a peptide consisting of 38 amino acid residues which enhances adenylate cyclase activity, is one such peptide whose expression mechanism was unknown in the prior art.

Promoter regions, typically located upstream from genes, are activated by factors which result in the synthesis of mRNA coding for the protein.

Some factors which activate promoter regions have been reported. However, most of them are specific to the cells which specifically express the protein.

Human PACAP is a protein secreted by nerve cells and is specifically produced in the hypothalamas. Accordingly, a promoter of human PACAP can possibly produce substances specific to nerve cells.

SUMMARY OF THE INVENTION

The present inventors have undertaken the study of the mechanism of the expression of the human PACAP38 gene in order to develop methods for inducing the expression. Their study has led to the isolation of genomic DNA of PACAP38 from a human DNA library and the determination of its nucleotide sequence. This has made it possible to induce human PACAP38 through genetic engineering techniques, thus achieving the present invention.

Concurrently, the present inventors have further cloned the gene of human PACAP38, which has been compared with the structure of the previously cloned cDNA of human PACAP38 to determine the structure thereof and to elucidate the relationship between an intron and an exon. At the same time, a promoter region essential for the expression of the gene has been determined.

In accordance with the present invention, there are provided (1) a genomic DNA of human PACAP38; (2) a DNA containing a DNA sequence coding for human PACAP38; (3) a DNA of human PACAP38 promoter; (4) a transformant carrying a vector which contains a DNA of (3) or further contains a DNA coding for a protein downstream from the promoter; and (5) a method for preparing a protein comprising cultivating the transformant described in the above (4), accumulating the protein in a culture product, and collecting the resulting protein such as mature PACAP38.

The present invention further provides a method of producing substances specifically produced in nerve cells, such as human PACAP38. In the method, an expression vector is constructed containing a cDNA coding for a protein (e.g., PACAP38), specifically expressed in nerve cells, (e.g., astrocytes), is linked downstream from the promoter of the present invention. The expression vector is then introduced into the cultured cell, for example, astrocytes to produce the proteins specifically produced in nerve cells, such as PACAP. The promoter of the present invention can also be used for neuroscientific study regarding the production of substances in astrocytes, differentiation of the cells, morphological change of the cells and growth of the cells.

BRIEF DESCRIPTION OF THE DRAWINGS

FIG. 1 is a simplified restriction enzyme map of a genomic DNA of human PACAP38; and FIG. 2 [SEQ. ID. NO:1] shows a nucleotide sequence of the genomic DNA of human PACAP38 and an amino acid sequence (SEQ. ID. NO: 2) of a human PACAP38 precursor from which a mature peptide can be deduced.

DESCRIPTION OF THE PREFERRED EMBODIMENTS

Figure 3:
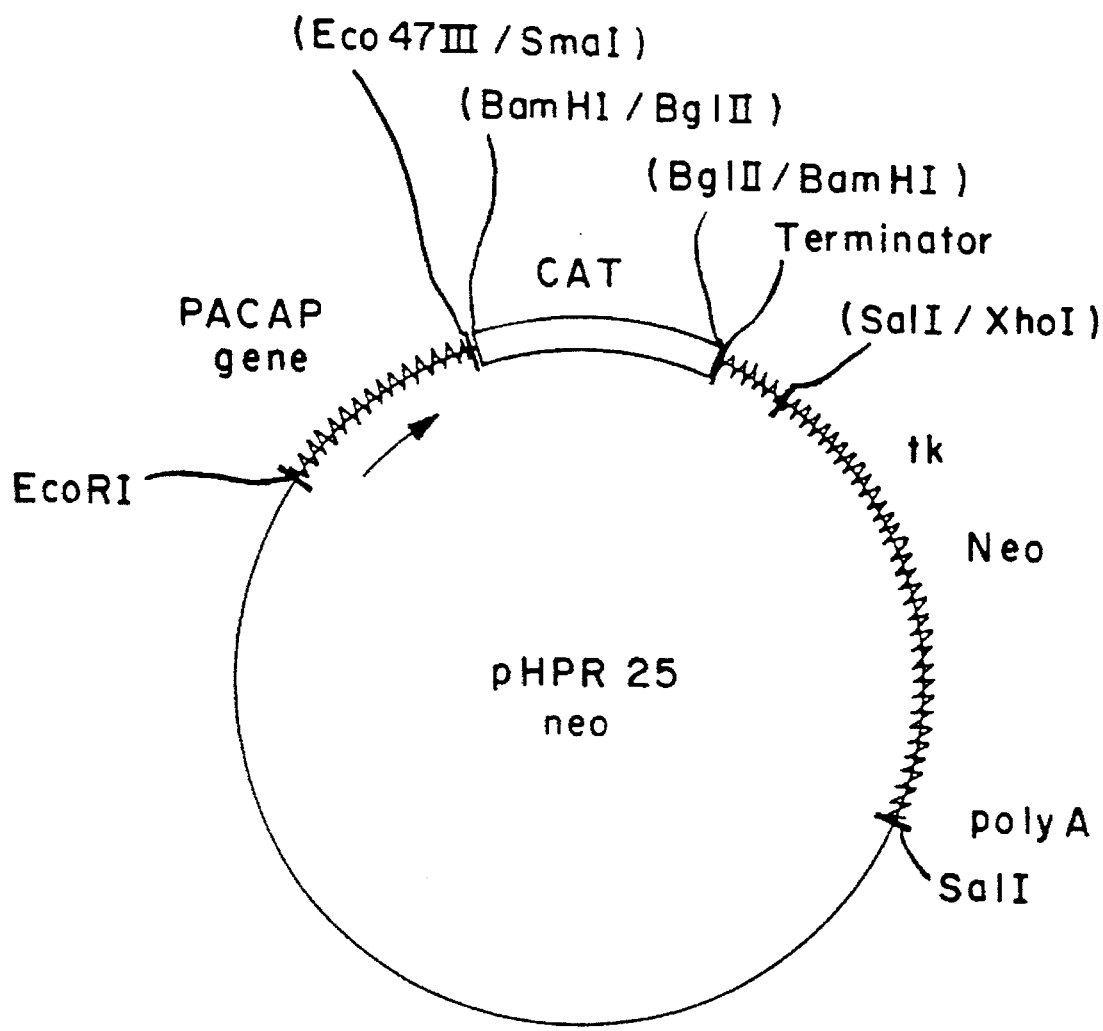
FIG. 3 shows a construction of a plasmid into which a 5'-region of human PACAP38 genomic DNA was introduced.

In the present invention, a DNA having the nucleotide sequence coding for the precursor protein of human PACAP38 or mature PACAP38 and for a promoter of human PACAP38 can be prepared, for example, by the following process:

(i) Human cell DNA is extracted and treated with restriction enzyme such as EcoRI or SalI, and is introduced into a phage or a plasmid;

(ii) The recombinant phage or plasmid thus obtained is introduced into an appropriate host cell to produce a transformant;

(iii) After cultivation of the transformant thus obtained, the plasmid or the phage containing the desired DNA is isolated from the transformant by an appropriate method such as hybridization with a DNA probe coding for a portion of PACAP38; and (iv) The desired cloned DNA is cut out from the recombinant DNA.

Methods for cloning the PACAP38 DNA from the human DNA library include, for example, the plaque hybridization method [T. Maniatis et al., *Molecular Cloning*, Cold Spring Harbor Laboratory (1982)] using as a probe an oligonucleotide chemically synthesized reflecting phage vector λgt11 or EMBL and the amino acid sequence of PACAP38, or the cDNA of PACAP38.

The PACAP38 cDNA thus cloned is subcloned to a plasmid such as pBR322, pUC12, pUC13, pUC18, pUC19, pUC118, pUC119 or the like to obtain the human PACAP38 DNA, if necessary.

The nucleotide sequence of the DNA thus obtained is determined, for example, by the Maxam-Gilbert method [A. M. Maxam and W. Gilbert, *Proc. Natl. Acad. Sci., U.S.A.* 74, 560 (1977)] or the dideoxy method [J. Messing et al., *Nucleic Acids Research* 9, 309 (1981)], and the existence of the human PACAP38 DNA is confirmed in comparison with the known amino acid sequence.

As described above, the DNA (FIG. 2, SEQ ID NO:1) containing a DNA fragment coding for a portion of the precursor protein of human PACAP38 is obtained.

The restriction enzyme fragment map of the DNA coding for the precursor protein of human PACAP38 is shown in FIG. 1. The nucleotide sequence of the DNA determined by the dideoxy method and the amino acid sequence deduced from that nucleotide sequence are shown in FIG. 2.

A DNA coding for a precursor protein of human PACAP38 cloned as described above is compared with a cDNA of human PACAP38 previously cloned, and then the relationship of introns and exsons of the gene is determined and a promoter region essential for an expression of the gene is deduced. A DNA sequence essential as a promoter is determined from the portion which covers a promoter region of human PACAP38.

For example, a region containing a DNA sequence of SEQ ID NO:3 can be used as the promoter. The promoter can be obtained from pHPR10neo obtainable from the transformant, *Escherichia coli* MV1184/pHPR10 neo (FERM BP-4084) according to a method of Example 3. A DNA fragment having a DNA sequence of the promoter of the present invention can be synthesized using the phosphoamidide method using standard DNA synthesizing equipment(Applied Biosystems Co. Ltd.).

The plasmids into which the DNA is introduced include, for example, pBR322 [*Gene* 2, 95 (1977)], pBR325 [*Gene* 4, 121 (1978)], pUC12 [*Gene* 19, 259 (1982)] and pUC13 [*Gene* 19, 259 (1982)], each derived from *Escherichia coli*, and pUB110 derived from *Bacillus subtilis* [*Biochemical and Biophysical Research Communication* 112, 678 (1983)]. However, any other plasmid can be used as long as it is replicable and viable in the host. The phage vectors into which the DNA is introduced include, for example, λgt11 [R. Young and R. Davis, *Proc. Natl. Acad. Sci., U.S.A.* 80, 1194 (1983)] and EMBL3 [Prischauf et al., *J. Mol. Biol.* 170, 827 (1983)]. However, any other phage vector can be used as long as it is replicable and viable in the host.

Methods for introducing the DNA into the plasmid include, for example, the method described in T. Maniatis et al., *Molecular Cloning*, p.239, Cold Spring Laboratory, (1982). Methods for introducing the DNA into the phage vector include, for example, the method of T. V. Hyunh et al. [*DNA Cloning, A Practical Approach* 1, 49 (1985)].

The plasmid thus obtained is introduced into the appropriate host cells such as Escherichia and Bacillus.

Examples of Escherichia described above include *Escherichia coli* K12DH1 [*Proc. Natl. Acad. Sci. U.S.A.* 60, 160 (1968)], M103 [*Nucleic Acids Research* 9, 309 (1981)], JA221 [*Journal of Molecular Biology* 120, 517, (1978)], HB101 [*Journal of Molecular Biology* 41, 459 (1969)] and C600 [*Genetics* 39, 440 (1954)].

Examples of Bacillus described above include *Bacillus subtilis* MI114 [Gene 24, 255 (1983)] and 207-21 [*Journal of Biochemistry* 95, 87 (1984)].

Methods for transforming the host with the plasmid include, for example, the calcium chloride method and the calcium chloride/rubidium chloride method described in T. Maniatis et al., *Molecular Cloning*, p.249, Cold Spring Harbor Laboratory, (1982).

When the phage vector is used, for example, the phage vector can be transduced into proliferated *E. coli*, using the in vitro packaging method.

In the present invention, an expression vector containing a DNA having the nucleotide sequence coding for the precursor protein of human PACAP38, mature PACAP38 or other protein can be prepared, for example, by the following process:

(i) Human cell DNA is extracted and treated with restriction enzyme such as EcoRI or SalI, and is introduced into a phage or a plasmid;

(ii) The recombinant phage or plasmid thus obtained is introduced into an appropriate host cell to produce a transformant;

(iii) After cultivation of the transformant thus obtained, the plasmid or the phage containing the desired DNA is isolated from the transformant by an appropriate method such as hybridization with a DNA probe coding for a portion of PACAP38;

(iv) The desired cloned DNA is cut out from the recombinant DNA; and (v) The cloned DNA or a portion thereof is ligated downstream from a promoter in a vector suitable for expression, whereby an expression vector can be obtained.

Expressible proteins other than PACAP38, include nerve cell-derived proteins such as Neuro Growth Factor(NGF), Brain Derived Neurotrophin-3(BDNT-3) and etc.

In obtaining a structural gene to be expressed, plasmids into which a DNA is incorporated, incorporation methods, hosts, transformation methods which are similar with the above-described ones can be used.

The region intended to be expressed is cut out from the cloned DNA and ligated downstream from the promoter in a vehicle (vector) suitable for expression, whereby the expression vector can be obtained.

The DNA has ATG as a translation initiating codon at the 5'-terminus thereof and may have TAA, TGA or TAG as a translation terminating codon at the 3'-terminus. Further, a consensus sequence reactive to cyclic AMP is observed upstream from ATG of the 5'-terminus. These translation initiating codons and translation terminating codon may be added by use of an appropriate synthetic DNA adaptor such as adaptor containing a translation initiating codon ATG or a translation terminating codon TAA, TAG or TGA.

The vectors include the above plasmids derived from *E. coli* such as pBR322, pBR325, pUC12 and pUC13, plasmids derived from *Bacillus subtilis* such as pUB110, pTP5 and pC194, plasmids derived from yeast such as pSH19 and pSH15, bacteriophages such as λ phage, and animal viruses such as retroviruses and vaccinia viruses.

As a promoter, a promoter of the present invention containing a DNA sequence of SEQ ID NO:3 can be used. The promoter can be obtained from pHPR10neo obtainable from the transformant, *Escherichia coli* MV1184/pHPR10 neo (FERM BP-4084) according to a method of Example 3.

Figure 5:
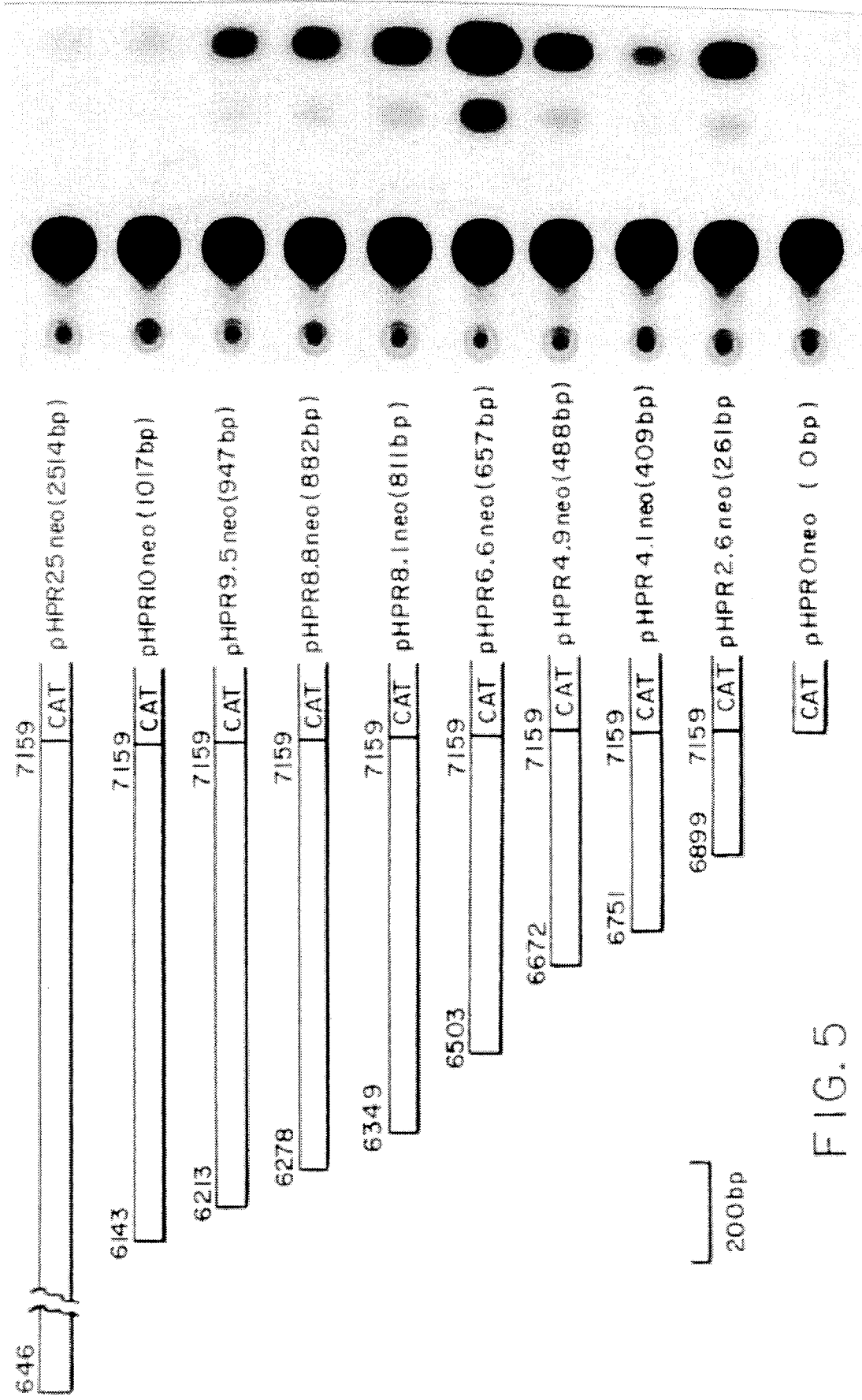
FIG. 5 shows promoter activity of some shorter DNA fragments located in a 5'-region of genomic DNA of human PACAP38.

Further, pHPR9.5neo, pHPR8.8neo, pHPR8.1neo, pHPR4.9neo, pHPR4.1neo and pHPR2.6neo as shown in FIG. 5 can also be used.

When the host is an animal cell, a SV40-derived promoter, a retrovirus promoter, a metallothionein promoter, a heat shock promoter or the like can be used. The use of an enhancer such as an SV40-derived enhancer, a retrovirus-derived enhancer, is also effective for expression.

By using a vector containing the DNA coding for the precursor protein of human PACAP38, the mature peptide PACAP38 or other protein thus constructed, the transformant is prepared.

Hosts for transformants include Escherichia and Bacillus described above, and animal cells.

Examples of the animal cells include monkey cell COS-7, Vero, Chinese hamster cell (CHO), mouse L cell, human FL cell and human nerve cell 1MR-32.

The transformation of Escherichia described above is conducted, for example, according to the method described in *Proc. Natl. Acad. Sci. U.S.A.*, 69, 2110 (1972), *Gene*, 17, 107 (1982) or the like.

The transformation of animal cells is carried out, for example, according to the method described in *Virology*, 52, 456 (1973).

Thus, the transformant transformed with the expression vector containing the DNA coding for the precursor protein of human PACAP38 or the mature peptide (PACAP38) is obtained.

When the animal cell transformants are cultivated, examples of the media which can be used include MEM medium containing about 5 to 20% fetal calf serum [*Science*, 122, 501 (1952)], DMEM medium [*Virology*, 8, 396 (1959)], RPMI1640 medium [*The Journal of the American Medical Association*, 199, 519 (1967)] and 199 medium [*Proceeding of the Society for the Biological Medicine*, 73, 1 (1950)]. The pH is preferably about 6 to about 8. The cultivation is usually carried out at about 30° to 40° C. for about 15 to about 60 hours, with aeration or agitation if necessary.

The gene product accumulated in a culture broth can be isolated and purified from the culture broth, for example, by the following method.

The collected cells are suspended in an appropriate buffer solution and disrupted by lysozyme such as zymolyace (Kirin Beer Co. Ltd) and/or mechanical disruption method using glass beads, and the desired substances are extracted. The buffer solution may contain a protein denaturant such as urea or guanidine hydrochloride, or a surface-active agent such as Triton X-100 for easier extraction.

The isolation and purification of the human PACAP38 precursor protein, mature peptide or other proteins contained in the culture supernatant or the exctracted solution thus obtained can be performed by an appropriate combination of isolating and purifying methods known in the art. The known isolating and purifying methods include methods utilizing solubility such as salt precipitation and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse phase high performance liquid chromatography and methods utilizing a difference in isoelectric point such as isoelectro-focussing electrophoresis.

Examples of the purification methods for proteins such as PACAP include a method described in Biochemical and Biophyrical Research Communications, 164,, No.1, p.567–574 (1989).

A system having a promoter of the present invention can express proteins specific to nerve cells or can be used to screen proteins specific to nerve cells.

Further, using an induction substance (chemical substance) for the PACAP gene, the amount of PACAP produced can be determined, for example, by the use of the sandwich EIA method. Furthermore, by using this assay system, it is possible to screen for chemical substances, e.g., drugs that are necessary for, or increase, production of PACAP. Substances showing promise during screening may be then given to experimental animals to understand their action, particularly on brain functions, more particularly on brain functions due to hormones. Moreover, the information thus obtained provides information which serves to elucidate human brain functions.

Such induction substances can also be screened in an assay using the promoter of the present invention operably linked in a vector to a gene encoding a marker protein such as chloramphenicol acetytransferase (CAT). Other suitable marker proteins include luciferase and alkaline phosphatase. Host cells, such as IMR-32 cells, are transformed with the vector using standard precedures. The resulting transformed cells are then exposed to a pre-determined induction substance, such as a drug or chemical, and the level of marker protein production is measured using methods standard for each marker. Substances capable of inducing or increasing marker protein expression can then be further evaluated.

The above methods may also be used to screen for substances that inhibit or decrease PACAP or marker protein expression.

The system employing a promoter of the present invention can express effectively PACAP38. Human PACAP38, including PACAP27, results in an increase in cAMP activity, and therefore can be utilized as therapeutic agents for growth and maintenance of human brain nerves.

There were hereinbefore described in detail the cloning of the DNA coding for human PACAP38, the preparation of the promoter activity expression vectors, the preparation of the transformants thereby, the production of a portion of human PACAP38 and the mature peptides by use of the transformants, and the utility thereof.

When the amino acids are capable of existing as optical isomers, it is understood that the L-forms are represented unless otherwise specified. When nucleotides, amino acids and so on are indicated by abbreviations in the specification and drawings, the abbreviations adopted by the IUPAC-IUB Commission on Biochemical Nomenclature or those commonly used in the art are employed. Accordingly, the following abbreviations are used.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
BHA: Benzhydrylamine
Cl-Z: 2-Chloro-benzyloxycarbonyl
Br-Z: 2-Bromo-benzyloxycarbonyl
Bzl: Benzyl
OBzl: Benzyl ester
HOBt: 1-Benzotriazole
DCC: N,N'-Dichlorohexylcarbodiimide
Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Asp or D: Aspartic acid
Lys or K: Lysine
Arg or R: Arginine
His or H: Histidine
Phe or F: Phenylalanine
Tyr or Y: Tyrosine
Trp or W: Tryptophan
Pro or P: Proline
Asn or N: Asparagine
Gln or Q: Glutamine With respect to the human PACAP38 precursor proteins or the mature peptide of the present invention, a portion of the amino acid sequence may be modified, through addition, elimination of amino acid(s) or substitution with other amino acid(s).

The present invention will be described in more detail with the following Reference Examples and Examples. It is understood of course that these Reference Examples and Examples are not intended to limit the scope of the invention.

Transformants E. coli MV1184/pHGP2312 and MV1184/pHGP2306 obtained in Example 2 described below were deposited with the Fermentation Research Institute, the Agency of Industrial Science and Technology, the Ministry of International Trade and Industry, Japan (FRI) under the accession number FERM BP-3054 on Aug. 10, 1990, and under the accession number FERM BP-3033 on Jul. 30, 1990, respectively. These microorganisms were also deposited with the Institute for Fermentation, Osaka, Japan (IFO) under the accession numbers IFO 15068 and IFO 15067, respectively, on Jul. 24, 1990.

Transformant E. coli MV1184/pGPR10neo in Example 3 described below was deposited with FRI under the accession number FERM BP-4084 on Nov. 26, 1992.

REFERENCE EXAMPLE 1

The amino acid sequence of sheep PACAP38 is believed to be identical to that of human PACAP38. When PACAP38 purified from sheep hypothalami (hereinafter, "Nat. 38p") and synthesized PACAP38 (hereinafter, "Syn.38p") were allowed to act on rat pituicytes in vitro, an increase in adenylate cyclase activity was identified by observing an increase of cAMP observed. The result is shown in Table 1. The minimum effective amount was $10^{-12}$M, and it was shown that the activity increased with increasing concentration.

Further, similar activity was also observed for synthesized 27-$NH_2$, the amino acids situated in the 132nd to 158th positions of FIG. 2 (hereinafter, "Syn.27p-$NH_2$"). In contrast, a similar increase in activity could not be observed for a synthesized porcine vasoactive intestinal polypeptide (hereinafter, Syn. pVIP).

TABLE 1

| Adenylate Cyclase Stimulating Test in Rat Pituicyte Culture | |
|---|---|
| | cAMP p mol/ml (M ± SEM) |
| Experiment 1 | |
| Syn.pVIP $10^{-12}$M | 1.35 ± 0.05 |
| Syn.pVIP $10^{-11}$M | 1.40 ± 0.00 |
| Syn.pVIP $10^{-10}$M | 1.45 ± 0.15 |
| Syn.pVIP $10^{-9}$M | 1.75 ± 0.05 |
| Syn.pVIP $10^{-8}$M | 2.55 ± 0.25 |
| Syn.pVIP $10^{-7}$M | 3.30 ± 0.20 |
| Control (Blank) | 1.55 ± 0.15 |
| Experiment 2 | |
| Syn.27p-$NH_2$ $10^{-12}$M | 2.05 ± 0.15 |
| Syn.27p-$NH_2$ $10^{-11}$M | 2.55 ± 0.15 |
| Syn.27p-$NH_2$ $10^{-10}$M | 4.00 ± 0.20 |
| Syn.27p-$NH_2$ $10^{-9}$M | 7.90 ± 0.30 |
| Syn.27p-$NH_2$ $10^{-8}$M | 9.20 ± 0.00 |
| Syn.27p-$NH_2$ $10^{-7}$M | 9.20 ± 0.20 |
| Syn.38p $10^{-12}$M | 2.15 ± 0.05 |
| Syn.38p $10^{-11}$M | 3.05 ± 0.35 |
| Syn.38p $10^{-10}$M | 4.60 ± 0.20 |
| Syn.38P $10^{-9}$M | 6.20 ± 0.10 |
| Syn.38p $10^{-8}$M | 8.60 ± 0.20 |
| Syn.38p $10^{-7}$M | 8.70 ± 0.20 |
| Nat.38p $10^{-12}$M | 1.50 ± 0.10 |
| Nat.38p $10^{-11}$M | 1.75 ± 0.05 |
| Nat.38p $10^{-10}$M | 2.60 ± 0.10 |
| Nat.38P $10^{-9}$M | 4.60 ± 0.00 |
| Nat.38p $10^{-8}$M | 8.05 ± 0.35 |
| Control (Blank) | 1.35 ± 0.05 |

REFERENCE EXAMPLE 2

The materials used in Reference Example 1 were similarly allowed to act on rat pituicytes in vitro. As a result, the releasing activity of prolactin (PRL), ACTH and GH was confirmed therein.

EXAMPLE 1

Preparation of cDNA Probe Coding for Human PACAP38

The cDNA of cloned human PACAP38 was labelled by the random prime method using $^{32}$P-dCTP for use in screening of the human genomic DNA library.

EXAMPLE 2

Isolation of Human PACAP Genomic DNA and Determination of Nucleotide Sequence Thereof

*E. coli* LE392 was infected with a human leukocyte-derived DNA library (Clontech Laboratories, Inc., Catalog No. HL1006d) and plated to cause phage plaques to appear. A portion of plaque DNA was transferred to a nitrocellulose film according to the method of W. Benton and R. Davis [*Science* 196, 180–182 (1977)] and hybridized with the cDNA probe labeled with $^{32}$p in Example 1. Hybridization was carried out in the absence of formaldehyde at 60° C. Clones positive to hybridization were isolated. Then, a cDNA portion of λHGP23, which was one of the clones described above, was cut out with SalI and recloned into the SalI site of plasmid pUC18 to prepare plasmids pHGP2312 and pHGP2306. By transforming *E. coli* MV1184 with these plasmids, transformants *E. coli* MV1184/pHGP2312 (FERM BP-3054) and *E. coli* MV1184/pHGP2306 (FERM BP-3033) were obtained. The cDNA portions included in these plasmids were 11.1 kbp and 6 kbp, respectively. The simplified restriction enzyme maps thereof are shown in FIG. 1. In the figure, black box (■) shows a mature human PACAP38 code region. The nucleotide sequence of this DNA portion was determined by the method of Sanger [*Proc. Natl. Acad. Sci. U.S.A.* 74, 5463–5467 (1977)]. This nucleotide sequence is shown in FIG. 2. The region from amino acid Nos. 132 to 169 is the mature peptide portion of human PACAP38.

Referring to FIG. 2, the 7540th to 7650th nucleotides form the first exon, which codes for amino acid residues M(1) to R(37) in the lower row. The amino acid numbers are designated in parentheses. The 9814th to 9945th nucleotides form the second exon, which codes for amino acid residues P(38) to R(81). The 10421st to 10519th nucleotides form the third exon, which codes for amino acid residues D(82) to G(114). The 11602nd to 11787th nucleotides form the fourth exon, which codes for amino acid residues G(115) to L(176).

Analysis of the genomic DNA revealed that the precursor of human PACAP38 consisted of 176 amino acid residues (SEQ ID NO:2).

EXAMPLE 3

Plasmid pHGP 2312 into which 5'-region of a genomic DNA of the cloned human PACAP had been incorporated was digested with EcoRI and Eco47III to obtain a DNA fragment of 2.5 kb (4646 to 7159 nucleotides). The DNA fragment was inserted into puc118 at the sites of EcoRI and SmaI.

A terminater of SV40 of 519 bp (to 0.52 Kbp) was incorporated at the sites of BamHI and SalI of the above described plasmid, and then a gene of chloramphenicol acetytransferase was incorporated into BamHI site of the plasmid.

A DNA fragment (pMCIneo.polyA, Stragene, USA) which has a promoter of thymidine kinase and a polyA signal.neomycin resistance gene was linked at SalI site of the above-described plasmid to construct a plasmid of FIG. 3.

FIG. 3 shows a plasmid into which a 2.5 kb of PACAP gene.

The plasmids which have each 2.2 kb, 1.5 kb and 1 kb of PACAP gene were named pHPR22neo, pHPR15neo. and pHPR10neo, respectively. Each 50 μg of the purified plasmids was applied to IMR-32 cells, neuroblastoma, grown up in a petri dish of 9 cm diameter with calcium phosphate method(Graham, PL1973, Virology 52, 456–457), which were cultivated in Eagles' MEM (EMEM) medium with 10% serum containing 0.5mg/ml of G418. The survived cells were further cultivated. The CAT assay according to Gorman et al (Mol. Cell. Biol., 2, 1044) was used.

Figure 4:
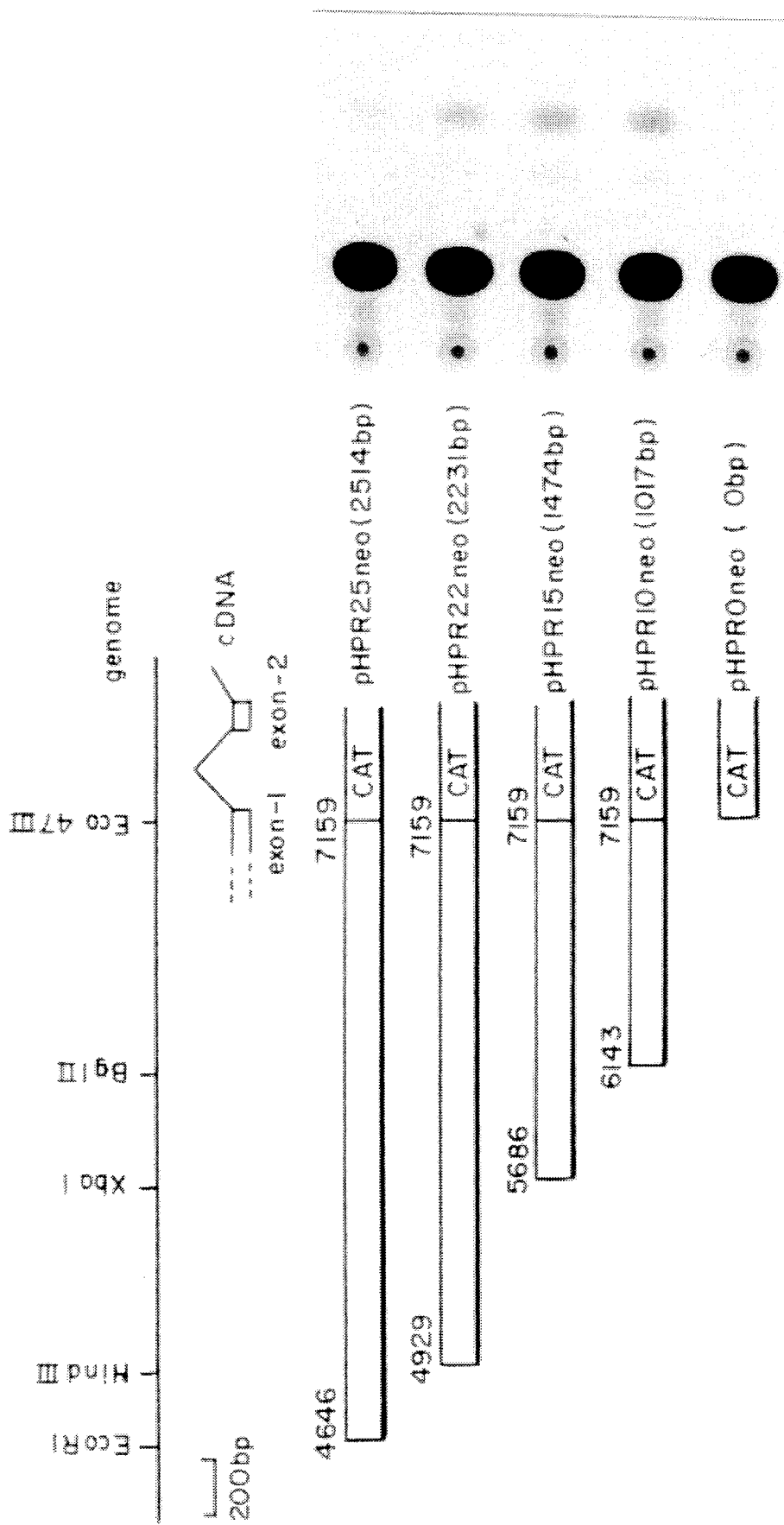
FIG. 4 shows promoter activity of various DNA fragments from 2.5 to 1 kb located in a 5'-region of genomic DNA of human PACAP38.

Each plasmid was applied to IMR-32 cells and CAT produced in the cells was assayed. The results are shown in FIG. 4. The black bands indicated by an arrow show CAT amount expressed. The stronger the black is, the more CAT is expressed, which means stronger promoter activity.

Plasmids into which DNA fragments of 2.5 kb to 1.0 kb of PACAP were incorporated respectively were found to produce CAT. Among them, the plasmid which has a 1 kb fragment had the highest activity and a promoter on the gene of human PACAP was shown to be located in a 17 kb nucleotide sequence of 6143rd to 7159th previously cloned.

A plasmid into which a further shortened PACAP gene was incorporated was constructed and the resulting plasmid was applied to IMR-32 cells to assay CAT produced. The plasmid pHPRneo6.6 (657 bp, 6503rd to 7159th nucleotides)(SEQ ID NO:3) had the highest activity as shown in FIG. 5.

The above results show that the promoter region is located in an EcoRI to Eco47III region of the PACAP gene (4644th to 7159th nucleotides). The promoter region deduced from the results can be used for an expression system utilizing nerve cells.

EXAMPLE 4

Synthesis of PACAP38 NH$_2$

PACAP38 NH$_2$ was synthesized by using 1.04 g (0.5 mmole) of a commercially available p-methyl BHA resin (Applied Biosystems Inc., California USA) and a peptide synthesizer (Model 430A, Applied Biosystems Inc.).

A starting amino acid, Boc-Lys(Cl-Z), was activated with HOBt/DCC and then condensed to the resin. Thereafter, the Boc group on the resin was treated with 50% trifluoroacetic acid/methylene chloride to deprotect the amino group. To this free amino group, the following protected amino acids activated with HOBt/DCC were reacted in turn according to the amino acid sequence of PACAP3:

Boc-Asn, Boc-Lys(Cl-Z), Boc-Val, Boc-Arg(Tos),

Boc-Gln, Boc-Tyr(Br-Z), Boc-Gly, Boc-Leu, Boc-Ala,

Boc-Met, Boc-Ser(Bzl), Boc-Asp(OBzl), Boc-Thr(Bzl),

Boc-Phe, Boc-Ile and Boc-His(Tos)

After the completion of each reaction, the residual amino groups were acetylated with acetic anhydride to obtain 2.42 g of a protected PACAP38 NH$_2$ resin.

0.51 g of the resulting protected PACAP38 NH$_2$ resin was treated with 5 ml of hydrogen fluoride in the presence of 0.6 g of p-cresol at 0° C. for 60 minutes, followed by removal of excess hydrogen fluoride by distillation under reduced pressure. The treated resin was washed twice with 5 ml of ethyl ether, and then extracted with 6 ml of 50% aqueous acetic acid. The insoluble material was removed by filtration and washed with 5 ml of 50% aqueous acetic acid. The filtrate and the washings were combined, and the combined solution was concentrated under reduced pressure to 2 to 3 ml. The concentrated solution was applied to a Sephadex LH-20 column (2×90 cm) for elution with 50% acetic acid. The main fractions were collected, and then removed by distillation under reduced pressure. Then, the residue was dissolved in 100 ml of 0.1% aqueous trifluoroacetic acid. The resulting solution was subjected to a YMC-ODS AM120 S-50 resin column (2.6×7 cm) and eluted by a linear gradient of 0.1% aqueous trifluoroacetic acid and 50% acetonitrile containing 0.1% trifluoroacetic acid.

The main fractions were combined, followed by lyophilization. Thus, 60 mg of a white powder was obtained. This powder was dissolved in 20 ml of 0.05M aqueous ammonium acetate. The resulting solution was subjected to a CM-Cellulofine resin column (1×6 cm) and eluted by a linear gradient of ammonium acetate from 0.05M to 1M. The main fractions were combined. The combined solution was subjected to a YMC-ODS column (2.6×7 cm) again and eluted by a linear gradient of from 0% to 40% aqueous acetonitrile containing 0.1% trifluoroacetic acid. The fractions of 28% to 30% acetonitrile were collected, followed by lyophilization. 21.6 mg of a white powder was obtained. Anal. of amino acids:

Asp 2.90(3), Thr 0.84(1), Ser 2.10(3), Glu 2.21(2),
Gly 2.00(2), Ala 3.29(3), Val 3.19(3), Met 1.01(1),
Ile 0.87(1), Leu 2.19(2), Tyr 3.93(4), Phe 0.92(1),
Lys 7.18(7), His 0.96(1), Arg 4.19(4)
$(M+H)^+$ by mass spectrography (SIMS): 4530
HPLC elution time: 19.6 minutes
Column conditions
Column: YMC-ODS (AM-301, S-5 120A)
Eluent: A (0.1% aqueous trifluoroacetic acid)
   B (acetonitrile containing 0.1% trifluoroacetic acid)
A linear gradient elution from the eluent A to the eluent B for 50 minutes
Flow rate: 1.0 ml/minute

EXAMPLE 5

Synthesis of PACAP27 $NH_2$

PACAP27 $NH_2$ was synthesized by using 1.04 g (0.5 mmole) of a commercially available p-methyl BHA resin (Applied Biosystems Inc.) and a peptide synthesizer (Model 430A, Applied Biosystems Inc.).

A starting amino acid, Boc-Leu, was activated with HOBt/DCC and then condensed to the resin. Thereafter, the Boc group on the resin was treated with 50% trifluoroacetic acid/methylene chloride to deprotect the amino group. To this free amino group, the following protected amino acids activated with HOBt/DCC were reacted in turn according to the amino acid sequence of PACAP38 (1–27):

Boc-Val, Boc-Ala, Boc-Leu, Boc-Tyr(Br-Z), Boc-Lys(Cl-Z), Boc-Met, Boc-Gln, Boc-Arg(Tos), Boc-Ser(Bzl), Boc-Asp(OBzl), Boc-Thr(Bzl), Boc-Phe, Boc-Ile and Boc-His(Tos)

After the completion of each reaction, the residual amino groups were acetylated with acetic anhydride to obtain 2.31 g of a protected PACAP27 $NH_2$ resin.

0.50 g of the resulting protected PACAP27 $NH_2$ resin was treated with 5 ml of hydrogen fluoride in the presence of 0.6 g of p-cresol at 0° C. for 60 minutes, followed by removal of excess hydrogen fluoride by distillation under reduced pressure. The treated resin was washed twice with 5 ml of ethyl ether, and then extracted with 6 ml of 50% aqueous acetic acid. The insoluble material was removed by filtration and washed with 5 ml of 50% aqueous acetic acid. The filtrate and the washings were combined, and the combined solution was concentrated under reduced pressure to 2 to 3 ml. The concentrated solution was applied on a Sephadex LH-20 column (2×90 cm) for elution with 50% acetic acid. The main fractions were collected, followed by removal by distillation under reduced pressure. 129 mg of a white powder was obtained. This powder was dissolved in 5 ml of 0.1% aqueous trifluoroacetic acid. The resulting solution was subjected to a TSK-GEL (ODS-120T) column (21.5× 300 mm) and eluted with 27% acetonitrile containing 0.1% aqueous trifluoroacetic acid.

The main fractions were collected, followed by lyophilization. 17.2 mg of a white powder was obtained. Anal. for amino acids:

Asp 1.99(2), Thr 0.98(1), Ser 2.76(3), Glu 1.25(1),
Gly 1.05(1), Ala 3.00(3), Val 1.56(2), Met 0.78(1),
Ile 0.72(1), Leu 1.88(2), Tyr 2.22(3), Phe 0.75(1),
Lys 2.73(3), His 1.51(1), Arg 1.94(2)
$(M+H)^+$ by mass spectrography (SIMS): 3145
HPLC elution time: 21.2 minutes
Column conditions
Column: YMC-ODS (AM-301, S-5 120A)
Eluent: A (0.1% aqueous trifluoroacetic acid)
   B (acetonitrile containing 0.1% trifluoroacetic acid)
A linear gradient elution from the eluent A to the eluent B for 50 minutes
Flow rate: 1.0 ml/minute

EXAMPLE 6

Using male Wistar rats having a body weight of 350 g under nembutal anesthesia, the hypotensive activity was measured. The value shows the decrease from normal value. The results are shown in Table 2.

TABLE 2

| | Hypotensive activity of PACAP | | |
|---|---|---|---|
| | Dosage (n mole/kg) | | |
| Compound | 0.3 | 1.0 | 3.0 |
| PACAP38 $NH_2$ | 3.2 ± 1.9 | 17.4 ± 2.4 | 29.8 ± 3.6 |
| | (n = 6) | (n = 6) | (n = 6) |
| PACAP27 $NH_2$ | 14.5 ± 3.1 | 51.9 ± 9.6 | 4.1 |
| | (n = 5) | (n = 5) | (n = 1) |

Unit: mm Hg

The following references, which are referred to for their disclosures at various points in this application, are incorporated herein by reference.

European Patent Publication 0 404 652 A1
Japanese Patent Application 1-155791/1990
Japanese Patent Application 1-259924/1990

What is claimed is:

1. An isolated DNA having the nucleotide sequence of SEQ ID NO: 3.

2. A vector in which a structural gene coding for a protein is operably linked downstream from the DNA of claim 1.

3. A vector according to claim 2 in which the protein is human pituitary adenylate cyclase activating polypeptide with 38 residues.

4. A transformant containing a vector according to claim 2 or 3.

5. A transformant according to claim 4, wherein the transformant is a prokaryotic host cell.

6. A transformant according to claim 4 wherein the transformant is an eukaryotic host cell.

7. A method for preparing a protein comprising:

1) cultivating a nerve cell containing a vector according to claim 2, or 3 under appropriate conditions for expression of the protein, 2) accumulating the protein in a culture broth; and 3) collecting the resulting accumulated protein.

8. A method according to claim 7, wherein the protein is human pituitary adenylate cyclase activating polypeptide with 38 amino acid residues.

9. The DNA of claim 1, wherein said DNA when operably linked to a gene directs expression of said gene in nerve cells.

* * * * *